(12) United States Patent
Oomori et al.

(10) Patent No.: US 7,372,557 B2
(45) Date of Patent: May 13, 2008

(54) SURFACE DEFECT INSPECTION APPARATUS AND SURFACE DEFECT INSPECTION METHOD

(75) Inventors: Takeo Oomori, Sagamihara (JP); Kazuhiko Fukazawa, Kamakura (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 11/508,298

(22) Filed: Aug. 23, 2006

(65) Prior Publication Data

US 2007/0046931 A1 Mar. 1, 2007

(30) Foreign Application Priority Data

Aug. 26, 2005 (JP) ............................. 2005-246206
Sep. 2, 2005 (JP) ............................. 2005-255121

(51) Int. Cl.
*G01N 21/00* (2006.01)
(52) U.S. Cl. .................................................. 356/237.1
(58) Field of Classification Search ...................... None
See application file for complete search history.

(56) References Cited

U.S. PATENT DOCUMENTS 5,764,363 A * 6/1998 Ooki et al. ................. 356/364

6,512,578 B1 * 1/2003 Komatsu et al. ......... 356/237.5

FOREIGN PATENT DOCUMENTS

JP A 2003-28621 1/2003

* cited by examiner

*Primary Examiner*—Tu T Nguyen
(74) *Attorney, Agent, or Firm*—Oliff & Berridge, PLC

(57) ABSTRACT

The present invention aims to provide a surface defect inspection apparatus and a surface defect inspection method for properly inspecting for a concave-shaped flaw (or a part thereof) substantially in parallel with a plane of incidence. The apparatus includes an illumination unit 10 illuminating a front surface (surface under inspection 5a) of an object to be inspected 5 with illumination light for inspection, a changing unit 1, 33 which relatively rotating the object to be inspected and the illumination unit around an axis AX1 perpendicular to the surface under inspection 5a and changing illumination conditions of the illumination light, a light reception unit 20 receiving scattered light emitted from the surface under inspection when illuminated with illumination light in each illumination condition, to capture images thereof, and a combining unit 32 combining images captured by the light reception unit to generate a combined image.

23 Claims, 11 Drawing Sheets

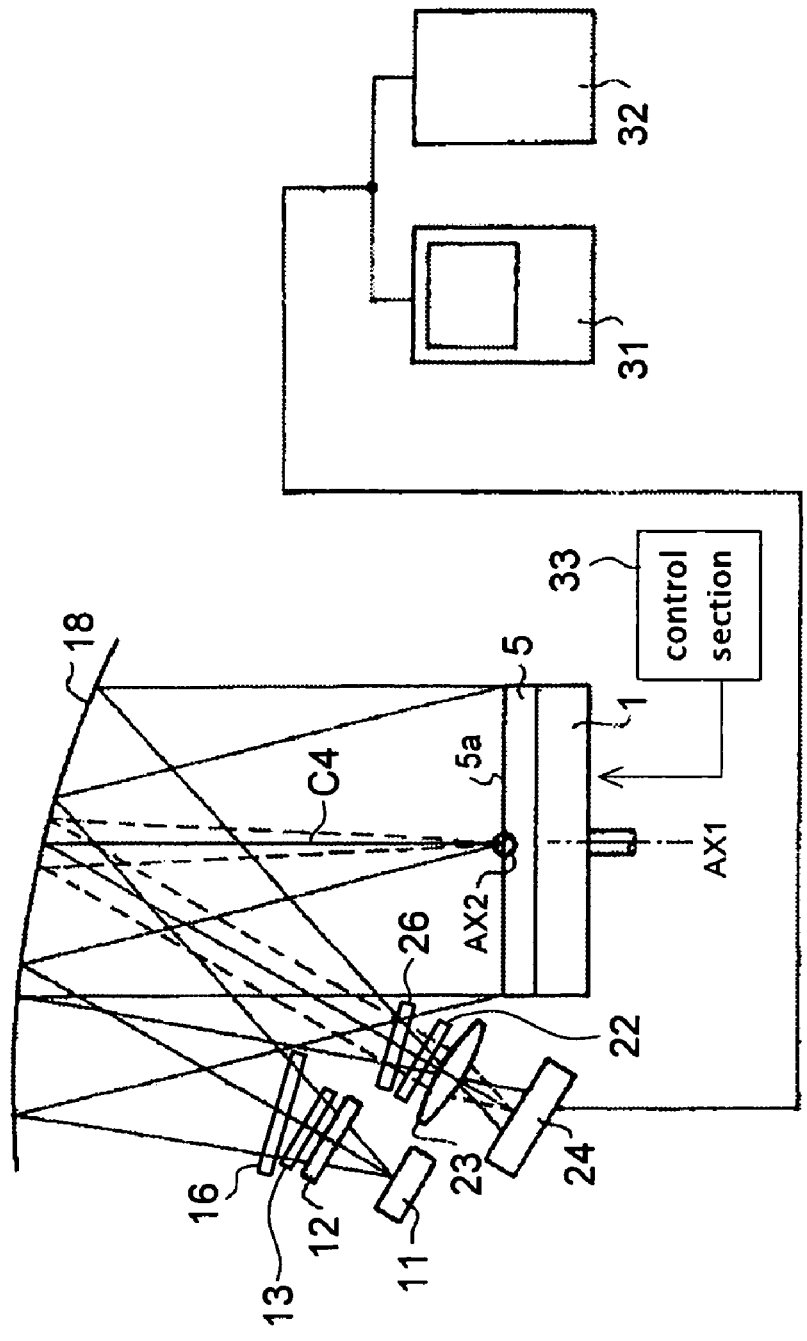
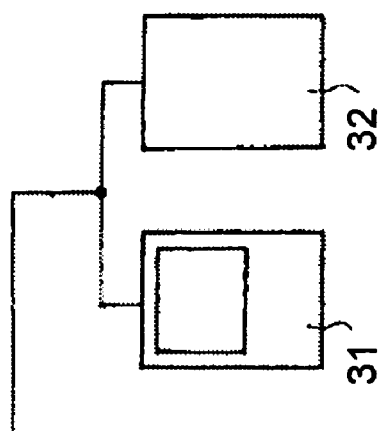
Fig. 8
400 (surface defect inspection apparatus)

Fig. 9
(a)
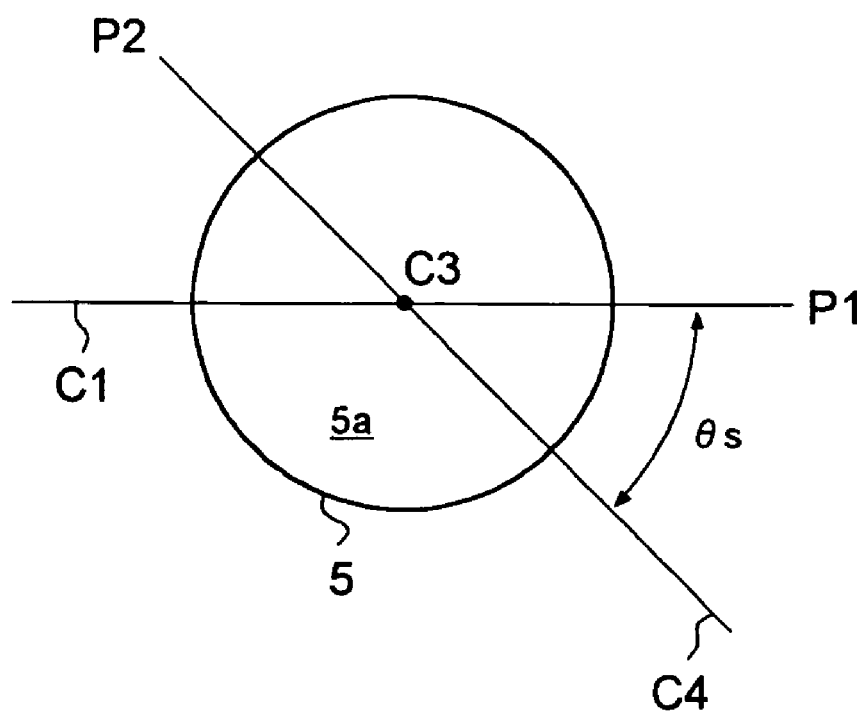
(b)
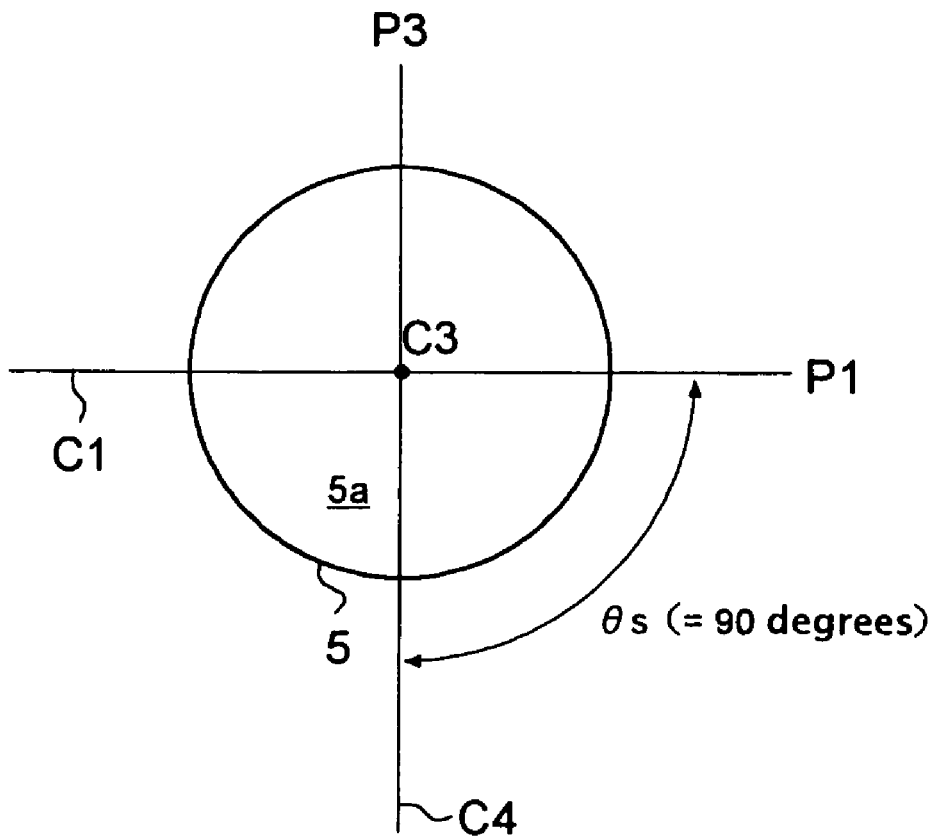

200 (surface defect inspection apparatus)

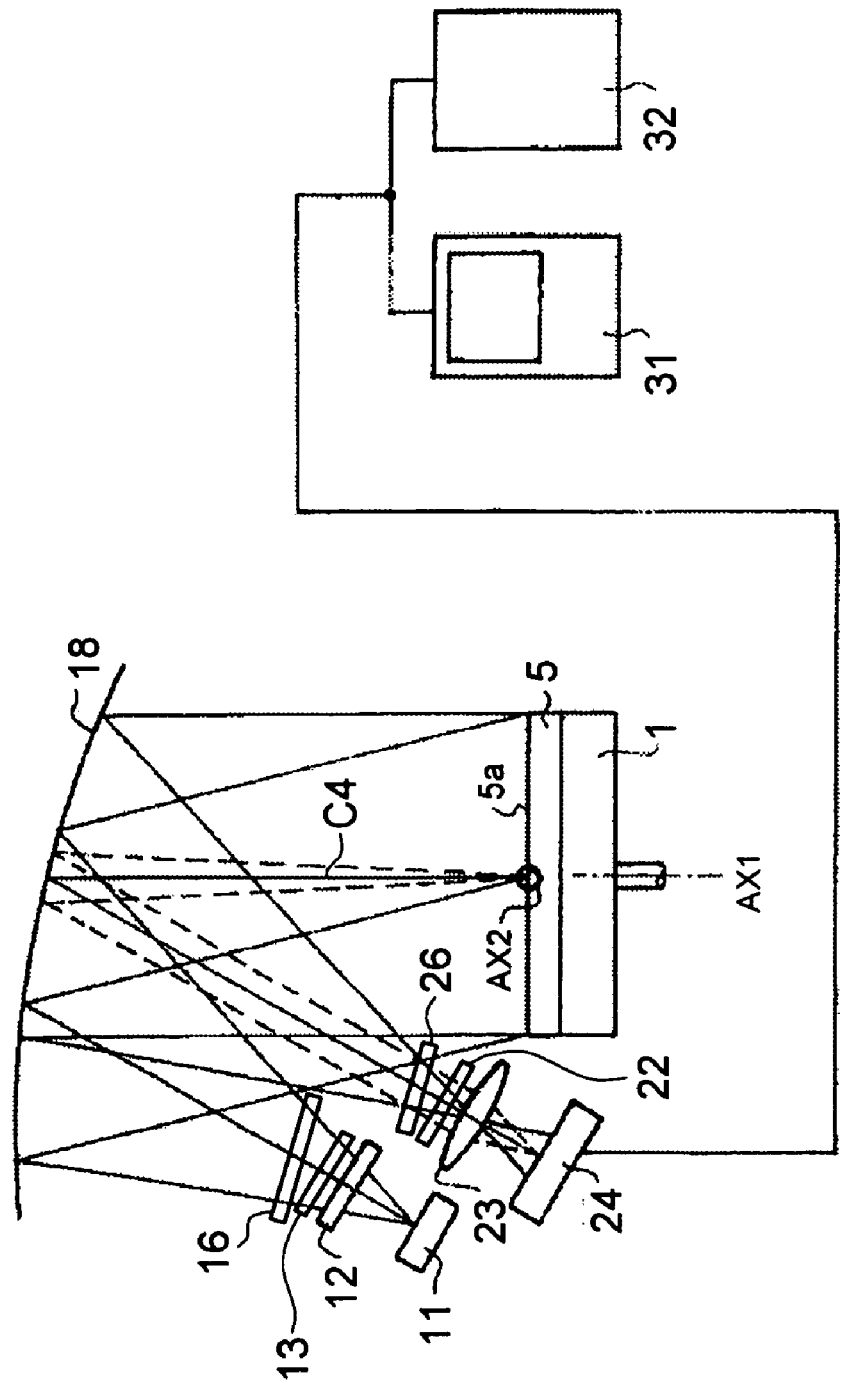
Fig. 13 (surface defect inspection apparatus)

SURFACE DEFECT INSPECTION APPARATUS AND SURFACE DEFECT INSPECTION METHOD

CROSS REFERENCE TO RELATED APPLICATION

This application is based upon and claims the benefit of the priority from Japanese Patent Application Nos. 2005-246206 and 2005-255121, each filed on Aug. 26, 2005 and Sep. 2, 2005, the entire contents of which are incorporated herein by reference.

BACKGROUND OF THE INVENTION

1. Field of the Invention

The present invention relates to a surface defect inspection apparatus and a surface defect inspection method for inspecting an object for a surface defect.

2. Description of the Related Art

An object of inspection such as a semiconductor wafer is inspected for a surface defect in such a manner that the object being rotated or shaken is visually inspected by an inspector while the front surface of the object is illuminated with illumination light at various angles. In recent years, to decrease fluctuation in inspection quality and improve labor saving and effectiveness of the inspection, techniques to automate this inspection have been studied (for example, refer to Japanese Unexamined Patent Application Publication No. 2003-28621). For inspecting for a surface defect, an apparatus disclosed therein illuminates an object to be inspected with illumination light and receives scattered light emitted from the front surface of the object to be inspected in a predetermined direction. In addition, it is proposed that angle conditions for an illumination system and a light reception system be adjusted to prevent reception of noise light (including specular light and diffracted light) other than scattered light.

However, there are various forms of surface defects on the objects to be inspected. When an object has a defect on the surface such as a concave-shaped flaw which is substantially in parallel with a plane of incidence including the illumination direction of the illumination light and the normal line of the front surface of the object, the above-mentioned apparatus cannot perform an inspection for the flaw properly since the intensity of scattered light emitted from the flaw is very weak. Moreover, if the concave-shaped flaw is curved and a part thereof is substantially in parallel with the plane of incidence, the apparatus cannot inspect for the entire flaw.

Furthermore, even in the angle conditions adjusted as described above, diffracted light may be insufficiently removed, or even if diffracted light is sufficiently removed, the intensity of scattered light may be weak. Thus, it may be not possible to secure an SN ratio necessary for the surface defect inspection.

SUMMARY OF THE INVENTION

Therefore, a first object of the present invention is to provide a surface defect inspection apparatus and a surface defect inspection method that can properly inspect for a concave-shaped flaw (or a part thereof) even if it is substantially in parallel with a plane of incidence.

A second object of the present invention is to provide a surface defect inspection apparatus and a surface defect inspection method that can surely remove diffracted light to secure an SN ratio necessary for inspecting for a surface defect.

A first surface defect inspection apparatus according to the present invention includes an illumination unit, a changing unit, a light reception unit, and a combing unit. The illumination unit illuminates a front surface of an object to be inspected with illumination light for inspection. The changing unit relatively rotates the object to be inspected and the illumination unit around an axis perpendicular to the front surface, to change illumination conditions of the illumination light. The light reception unit receives scattered light emitted from the front surface when the front surface is illuminated with the illumination light in each of the illumination conditions, to capture images of the front surface. The combing unit combines the images captured by the light reception unit in different illumination conditions, to generate a combined image.

It is preferred that in the first surface defect inspection apparatus, the changing unit relatively rotate the object to be inspected and the illumination unit at equal intervals within an angle range of 180 degrees or 360 degrees around the axis perpendicular to the front surface, to change the illumination conditions.

It is also preferred for the first surface defect inspection apparatus to include an image processing unit which processes the combined image generated by the combining unit to detect a defect on the front surface.

It is also preferred for the first surface defect inspection apparatus to include a display unit which displays the combined image generated by the combining unit.

It is preferred that in the first surface defect inspection apparatus, the light reception unit be set so as to satisfy the following conditional expressions (1) to (3):

$$\delta\theta o < (\theta r - \delta\theta r) \tag{1}$$

$$\theta r \leq 10 \text{ degrees} \tag{2}$$

$$\theta o \leq 60 \text{ degrees} \tag{3}$$

where $\theta o$ is an output angle of specular light emitted from the front surface when the front surface is illuminated with the illumination light; $\delta\theta o$ is an aperture angle of the specular light; $\theta r$ is an angle between an optical axis of the specular light and an optical axis of the light reception unit; and $\delta\theta r$ is an aperture angle of the light reception unit.

It is preferred that in the first surface defect inspection apparatus, the optical axis of the light reception unit be included in a same plane of incidence as those of the illumination unit and of the specular light, and that at least one of the object to be inspected, the illumination unit, and the light reception unit be rotatably supported around an axis which runs through an intersection of the optical axis of the illumination unit and the front surface and which is perpendicular to the plane of incidence.

It is also preferred for the first surface defect inspection apparatus to include a setting unit which rotates at least one of the object to be inspected, the illumination unit, and the light reception unit around the axis perpendicular to the plane of incidence, to set the output angle $\theta o$ of the specular light and the angle $\theta r$ of the optical axis of the light reception unit.

It is preferred that in the first surface defect inspection apparatus, the illumination light be substantially collimated light.

In addition, it is preferred that the illumination light be linearly polarized light and that the light reception unit receive a polarization component of scattered light emitted from the front surface, to capture the images. The polarization component is perpendicular to a plane of vibration of the linearly polarized light.

It is preferred that in the first surface defect inspection apparatus, the illumination unit and the light reception unit have telecentric structures on their respective sides facing to the front surface.

A surface defect inspection method according to the present invention includes the steps of illuminating, by an illumination unit, a front surface of an object to be inspected with illumination light for inspection; relatively rotating the object to be inspected and the illumination unit around an axis perpendicular to the front surface, to change illumination conditions of the illumination light; receiving scattered light emitted from the front surface when the front surface is illuminated with the illumination light in each of the illumination conditions, to capture images of the front surface; and combining the images captured at the light receiving step in different illumination conditions, to generate a combined image.

It is preferred that the condition changing step further include the step of relatively rotating the object to be inspected and the illumination unit at equal intervals within an angle range of 180 degrees or 360 degrees around the axis perpendicular to the front surface, to change the illumination conditions.

A second surface defect inspection apparatus according to the present invention includes an illumination unit and a light reception unit. The illumination unit illuminates a front surface of an object to be inspected with linearly polarized light. The light reception unit receives a polarization component of scattered light which is emitted from the front surface when the front surface is illuminated with the linearly polarized light. The polarization component is perpendicular to a plane of vibration of the linearly polarized light. The light reception unit is set so as to satisfy the following conditional expressions (1) to (3):

$$\delta\theta o < (\theta r - \delta\theta r) \quad (1)$$

$$\theta r \leq 10 \text{ degrees} \quad (2)$$

$$\theta o \leq 60 \text{ degrees} \quad (3)$$

where $\theta o$ is an output angle of specular light which is emitted from the front surface when the front surface is illuminated with the illumination light; $\delta\theta o$ is an aperture angle of the specular light; $\theta r$ is an angle between an optical axis of the specular light and an optical axis of the light reception unit; and $\delta\theta r$ is an aperture angle of the light reception unit.

It is preferred that In the second surface defect inspection apparatus that the optical axis of the light reception unit be included in a same plane of incidence as those of the illumination unit and of the specular light.

It is preferred that in the second surface defect inspection apparatus, the plane which includes the optical axis of the light reception unit and the optical axis of the specular light be inclined at a predetermined angle $\theta s$ to the plane which includes the optical axis of the illumination unit and the optical axis of the specular light.

It is preferred that in the second surface defect inspection apparatus, the predetermined angle $\theta s$ be 90 degrees.

It is preferred that in the second surface defect inspection apparatus, the object to be inspected be rotatably supported around the axis perpendicular to the front surface.

It is preferred that in the second surface defect inspection apparatus, the linearly polarized light be substantially collimated light.

It is preferred that in the second surface defect inspection apparatus, the illumination unit illuminate the entire front surface with the linearly polarized light at once and that the light reception unit receive a polarization component of scattered light which is emitted from the entire front surface, to capture an image of the entire front surface. The polarization component is perpendicular to a plane of vibration of the linearly polarized light.

It is preferred that in the second surface defect inspection apparatus, the illumination unit and the light reception unit have telecentric structures on their respective sides facing to the front surface.

It is also preferred for the second surface defect inspection apparatus to include an image processing unit which processes an image generated by the light reception unit to detect a defect on the front surface.

It is also preferred for the second surface defect inspection apparatus to include a display unit which displays an image generated by the light reception unit.

BRIEF DESCRIPTION OF DRAWINGS

The nature, principle, and utility of the invention will become more apparent from the following detailed description when read in conjunction with the accompanying drawings in which like parts are designated by identical reference numbers, in which:

FIG. 4 is a schematic diagram describing orientations of repetitive patterns formed on a surface under inspection 5a.

FIG. 8 is a schematic diagram showing a structure of a surface defect inspection apparatus 400 according to a fourth embodiment.

FIGS. 9(a), 9(b) are schematic diagram describing the relationship of an optical axis C1 of an illumination unit and an optical axis C4 of a light reception unit viewed from arrow III of FIG. 1 and FIG. 3.

FIG. 13 is a schematic diagram showing a structure of a surface defect inspection apparatus 400 according to an eighth embodiment.

DESCRIPTION OF THE PREFERRED EMBODIMENTS

First Embodiment

Next, with reference to FIG. 1 to FIG. 5, a first embodiment of the present invention will be described in detail.

Figure 1:
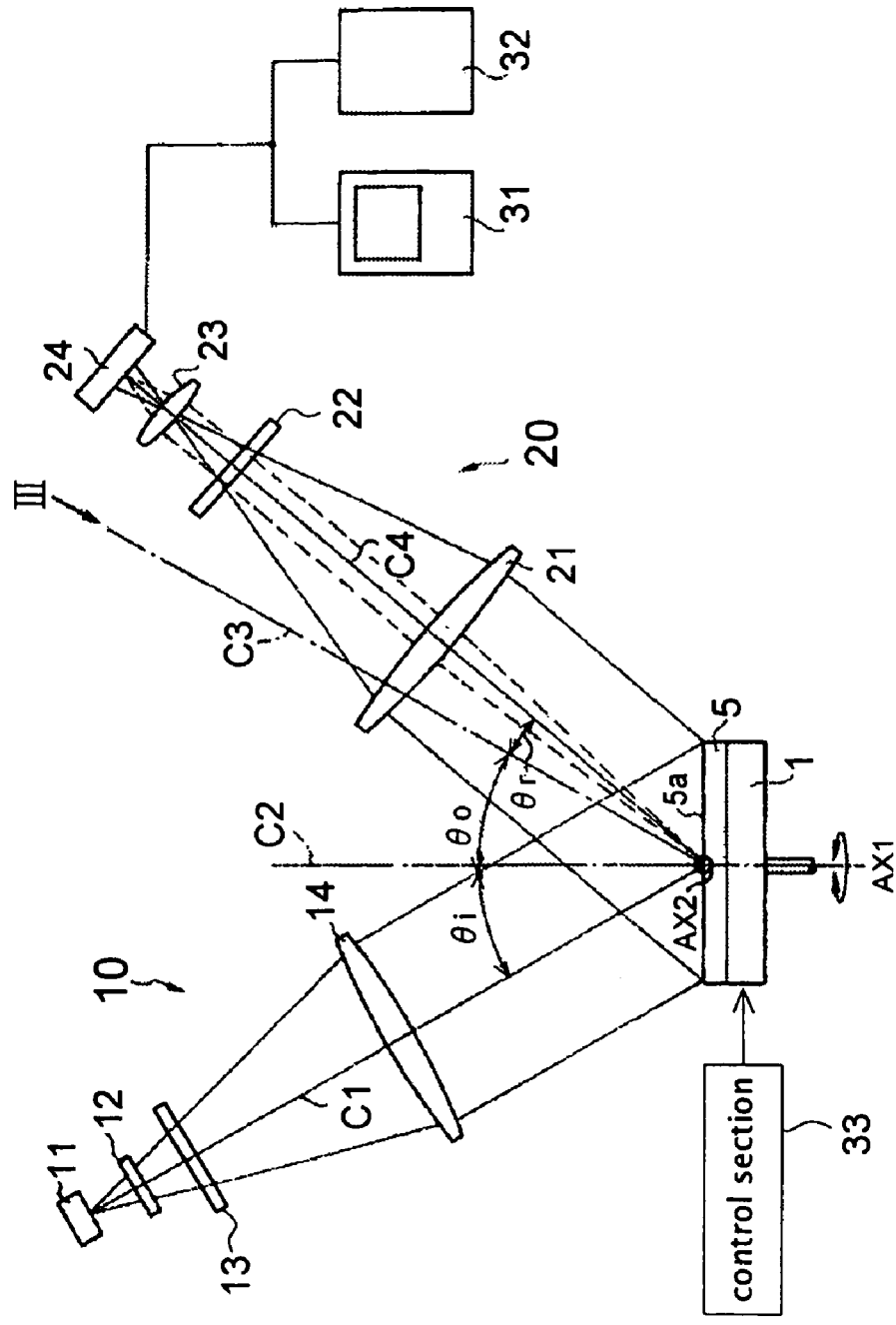
FIG. 1 is a schematic diagram showing a structure of a surface defect inspection apparatus 100 according to a first embodiment.

As shown in FIG. 1, a surface defect inspection apparatus 100 according to the first embodiment is made up of a support table 1 that supports an object to be inspected such as a semiconductor wafer, an illumination unit 10 that illuminates the front surface of the object to be inspected 5 (hereinafter, referred to as "the surface under inspection 5a") with illumination light for inspection, a light reception unit 20 that receives scattered light that is emitted from the surface under inspection 5a and captures an image of the surface under inspection 5a, a display unit 31 and an image processing unit 32 connected to the light reception unit 20, and a control section 33. The support table 1, the illumination unit 10, and the light reception unit 20 are disposed in a chamber (not shown).

The surface defect inspection apparatus 100 is a device that performs an inspection for a surface defect on an object to be inspected 5 in a fabrication process for an IC chip, a liquid crystal display panel, or the like. An IC chip and a liquid crystal display panel are made up of various types of circuit patterns layered on a semiconductor wafer or the like. The circuit patterns are formed, for example, by a photolithography processing. A flaw on the front surface (surface defect) of a semiconductor wafer in this process causes an operation failure of a final product. Thus, it is very important to perform an inspection for a surface defect in the fabrication process.

At an inspection for a surface defect, the object to be inspected 5 such as a semiconductor wafer is securely held by vacuum suction or the like in such a manner that the surface under inspection 5a on which circuit patterns and so forth have been formed is kept level. When the surface under inspection 5 is illuminated with illumination light for inspection emitted from the illumination unit 10, scattered light occurs on the surface under inspection 5a due to foreign matters such as dust or rubbish or convex- and concave-shaped flaws (they are in general referred to as "a surface defect"). Efficiently guiding the scattered light the light reception unit 20 enables a proper inspection for a surface defect on the object to be inspected 5.

However, since the surface under inspection 5a is a flat surface, specular light occurs on the surface under inspection 5a when illuminated with illumination light for inspection emitted from the illumination unit 1. In addition, many circuit patterns have been formed on the surface under inspection 5a. The circuit patterns contain wiring metal films (repetitive patterns having predetermined pitches) made of aluminum, copper, or the like. Thus, when the surface under inspection 5a is illuminated with the illumination light for inspection, diffracted light also occurs on the surface under inspection 5a depending on pitches of the repetitive patterns and so forth. These specular light and diffracted light are noise light.

According to the surface defect inspection apparatus 100 of the first embodiment, to securely remove noise light from the surface under inspection 5a and effectively guide scattered light to the light reception unit 20, angle conditions of the optical axis C1 of the illumination unit 10 and the optical axis C4 of the light reception unit 20 are adjusted as well as polarization units 13 and 22 are disposed in the illumination unit 10 and the light reception unit 20, respectively.

Figure 2:
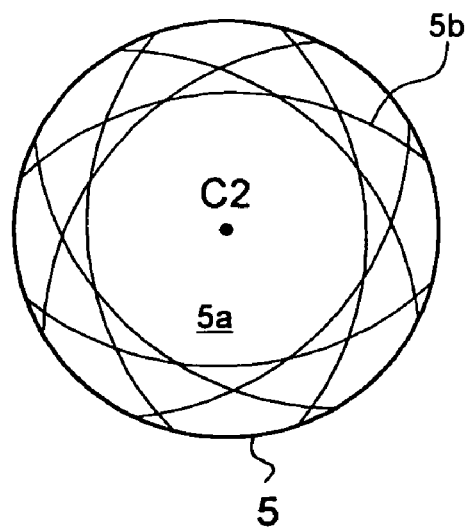
FIG. 2 is a schematic diagram describing an arc-shaped flaw 5b formed in a CMP treatment.

In order to properly inspect for many arc-shaped flaws 5b, as shown in FIG. 2, on the front surface (surface under inspection 5a) of the object to be inspected 5 which has been subjected to a CMP (Chemical Mechanical Polishing), the surface defect inspection apparatus 100 according to the first embodiment captures a plurality of images of the surface under inspection 5a and generates their combined image while changing illumination conditions of the illumination light for inspection.

Note that, the CMP treatment is a treatment to polish the surface under inspection 5a with a polish pad while rotating the object to be inspected 5. At this point, the polish pad is moved on the surface under inspection 5a so that the polish pad draws a circle having a larger radius of curvature than that of the surface under inspection 5a. Thus, when something causes insertion of a foreign matter between the polish pad and the surface under inspection 5a, many arc-shaped flaws 5b occur on the surface under inspection 5a. The arc-shaped flaws 5b tend to have a certain length and a concave-shape and be very shallow.

Next, the structure of the surface defect inspection apparatus 100 according to the first embodiment will be specifically described.

The support table 1 can be rotated on a horizontal plane around an axis AX1 that runs through the center of the surface under inspection 5a and extends in the vertical direction. When the illumination conditions of the illumination light for inspection to the surface under inspection 5a are changed, the support table 1 is rotated around the axis AX1 under the control of the control section 33.

In addition, the support table 1 can be rotated (shaken) around an axis AX2 that extends in the horizontal direction. The axis AX2 runs through the intersection of the optical axis C1 of the illumination unit 10 and the surface under inspection 5a and is perpendicular to a plane formed by the optical axis C1 of the illumination unit 10 and a normal line C2 of the surface under inspection 5a (hereinafter, this plane is referred to as "the plane of incidence P1"). When the angle conditions of the optical axis C1 of the illumination unit 10 and so forth are adjusted, the support table 1 is rotated around the axis AX2.

The illumination unit 10 is made up of a light source 11, a wavelength selection unit 12, a polarization unit 13, and an illumination lens 14. The optical axis C1 of the illumination unit 10 is inclined to the normal line C2 of the surface under inspection 5a. The angle between the optical axis C1 and the normal line C2, namely incident angle θi, is set so that the following conditional expression (4) is satisfied.

$$\theta i \leq 60 \text{ degrees} \tag{4}$$

The incident angle θi of the optical axis C1 of the illumination unit 10 can be set by rotating (shaking) the support table 1 around the axis AX2. Instead, the incident angle θi of the optical axis C1 of the illumination unit 10 may be set by rotating (shaking) the illumination unit 10 around the axis AX2 instead of the rotation of the support table 1 (or in addition to the rotation of the support table 1).

Examples of the light source 11 include a metal halide lamp, a mercury lamp, and a halogen lamp. The wavelength selection unit 12 selects a wavelength by changing various types of dichroic mirrors or interference mirrors. The wavelength selection unit 12 selectively allows light having a predetermined wavelength among light emitted from the light source 11 to pass.

Examples of the polarization unit 13 include a sheet film type polarization plate and a liquid crystal device. The polarization unit 13 converts light that is supplied from the wavelength selection unit 12 into linearly polarized light. The illumination lens 14 converts the linearly polarized light that is supplied from the polarization unit 13 into collimated light. The whole surface under inspection 5a is illuminated with the collimated light as the illumination light for inspection. The illumination unit 10 has a telecentric structure that faces the surface under inspection 5a.

Thus, the whole surface under inspection 5a is illuminated with the linearly polarized light (illumination light for inspection) emitted from the illumination unit 10. The direction of the plane of vibration of the linearly polarized light is set in parallel with or perpendicular to the plane of incidence P1 by the polarization unit 13. Instead, the direction of the plane of vibration of the linearly polarized light may be inclined to the plane of incidence P1. The wavelength of the linearly polarized light is set by the wavelength selection unit 12. The incident angle of the linearly polarized light is equivalent to the incident angle $\theta i$ of the optical axis C1 of the illumination unit 10. The incident angle of the linearly polarized light is constant on the whole surface under inspection 5a.

When the surface under inspection 5a is illuminated with the linearly polarized light, specular light is emitted therefrom in a direction of an optical axis C3 at an output angle $\theta o$. The output angle $\theta o$ is an angle between the optical axis C3 of the specular light and the normal line C2 of the surface under inspection 5a. Thus, the output angle $\theta o$ is equal to the incident angle $\theta i$ of the linearly polarized light. As a result, when the incident angle $\theta i$ satisfies the foregoing conditional expression (4), the output angle $\theta o$ satisfies the following conditional expression (5).

$$\theta o \leq 60 \text{ degrees} \quad (5)$$

The light reception unit 20 is made up of a first light reception lens 21, a polarization unit 22, a second light reception lens 23, and a CCD image sensor 24. The optical axis C4 of the light reception unit 20 is inclined to the optical axis C3 of the specular light. The angle between the optical axis C4 of the light reception unit 20 and the optical axis C3 (namely, an angle $\theta r$ between the optical axis C3 and the optical axis C4) is set so that the following conditional expression (6) is satisfied.

$$\theta r \leq 10 \text{ degrees} \quad (6)$$

The optical axis C4 of the light reception unit 20 is contained in the same plane of the optical axis C1 of the illumination unit 10 and the optical axis C3 of the specular light. This plane is equivalent to the plane of incidence P1 and is in parallel with the drawing of FIG. 1.

Figure 3:
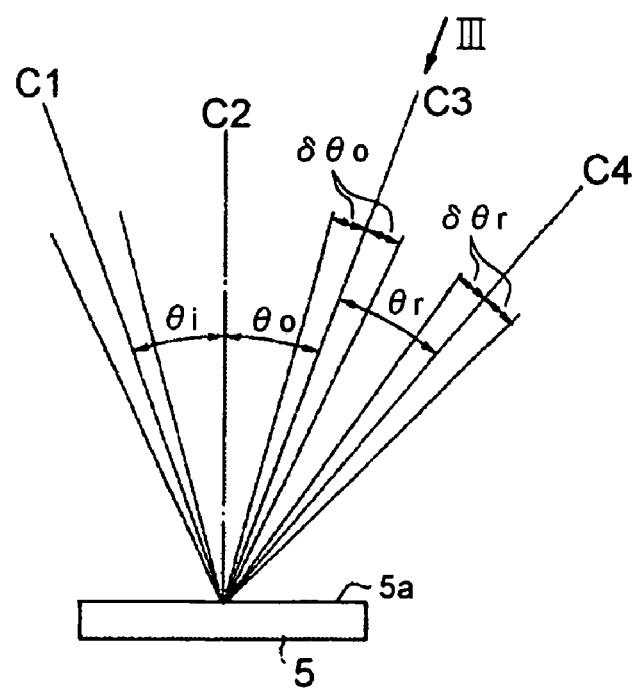
FIG. 3 is a schematic diagram describing the relationship of directions of individual optical axes and aperture angles.

As shown in FIG. 3, even if the specular light spreads in a circular cone shape around the optical axis C3 at an aperture angle $\delta\theta o$, the angle $\theta r$ of the optical axis C4 is set so that the aperture angle $\delta\theta o$ does not overlap with an aperture angle $\delta\theta r$ around the optical axis C4 of the light reception unit 20, namely the following conditional expression (7) is satisfied.

$$\delta\theta o < (\theta r - \delta\theta r) \quad (7)$$

When the conditional expression (7) is satisfied, the specular light from the surface under inspection 5a does not enter the circularly conical shape light reception range (aperture angel $\delta\theta r$) of the light reception unit 20. Thus, the light reception unit becomes a dirk field optical system relative to the specular light. In other words, specular light as one component of noise light not needed for inspection for a surface defect on the surface under inspection 5a can be securely removed.

When the incident angle $\theta i$ of the optical axis C1 of the illumination unit 10 is set, the output angle $\theta o$ of the specular light can be automatically obtained. In other words, when at least one of the support table 1 and the illumination unit 10 is rotated (shaken) around the axis AX2, the incident angle $\theta i$ and the output angle $\theta o$ can be set. In addition, the angle $\theta r$ of the optical axis C4 of the light reception unit 20 can be set by rotating (shaking) the light reception unit 20 around the axis AX2.

The light reception lenses 21 and 23 of the light reception unit 20 collect light (scattered light, specular light, diffracted light, and so forth) that is emitted from the surface under inspection 5a. Like the polarization unit 13, the polarization unit 22 is for example a polarization plate or a liquid crystal device. The polarization unit 22 allows a polarized light component perpendicular to the plane of vibration of the linearly polarized light as illumination light for inspection to pass therethrough (namely, the polarization unit 22 shuts out a horizontally polarized light component). In other words, the polarization unit 22 is disposed according to so-called Crossed Nichols. The light reception unit 20 has a telecentric structure that faces the surface under inspection 5a. The CCD image sensor 24 can capture an image of the whole surface under inspection 5a.

Specular light that is emitted from the surface under inspection 5a is one component of noise light not needed for inspection for a surface defect on the surface under inspection 5a. As described above, the specular light passes in a direction outside the light reception range of the aperture angle $\delta\theta r$ around the optical axis C4 of the light reception unit 20 (namely within the aperture angle $\delta\theta o$ around the optical axis C3). Thus, even if the specular light is collected by the first light reception lenses 21 and 23, the specular light does not enter the light reception plane of the CCD image sensor 24. In other words, the specular light can be securely removed.

On the other hand, diffracted light that is emitted from repetitive patterns of the surface under inspection 5a is one component of noise light that is not necessary to perform an inspection for a surface defect on the surface under inspection 5a. However, normally, the output direction of the diffracted light is different from that of the specular light. In addition, depending on the pitches of the repetitive patterns, the angle between the optical axis C3 of the specular light and the optical axis of the diffracted light may get close to the angle $\theta r$ of the optical axis C4 of the light reception unit 20. In this case, the diffracted light passes in the light reception range of the aperture angle $\delta\theta r$ around the optical axis C4. Unless the polarization unit 22 is disposed, the diffracted light enters the light reception plane of the CCD image sensor 24.

However, since the surface defect inspection apparatus 100 according to the first embodiment is provided with the polarization unit 22, it passes a polarized light component perpendicular to the plane of vibration of the linearly polarized light as illumination light for inspection (namely, the polarization unit 22 shuts out a polarized light component in parallel with the plane of vibration). Thus, even if the diffracted light that is emitted from the repetitive patterns on the surface under inspection 5a passes in the light reception range of the aperture angle $\delta\theta r$ around the optical axis C4 of the light reception unit 20, the polarization unit 22 shuts out the diffracted light so that it does not enter the light reception plane of the CCD image sensor 24.

Figure 4:
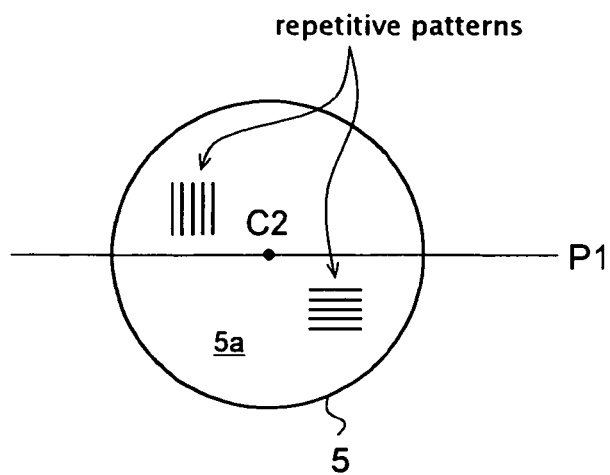
Figure 5:
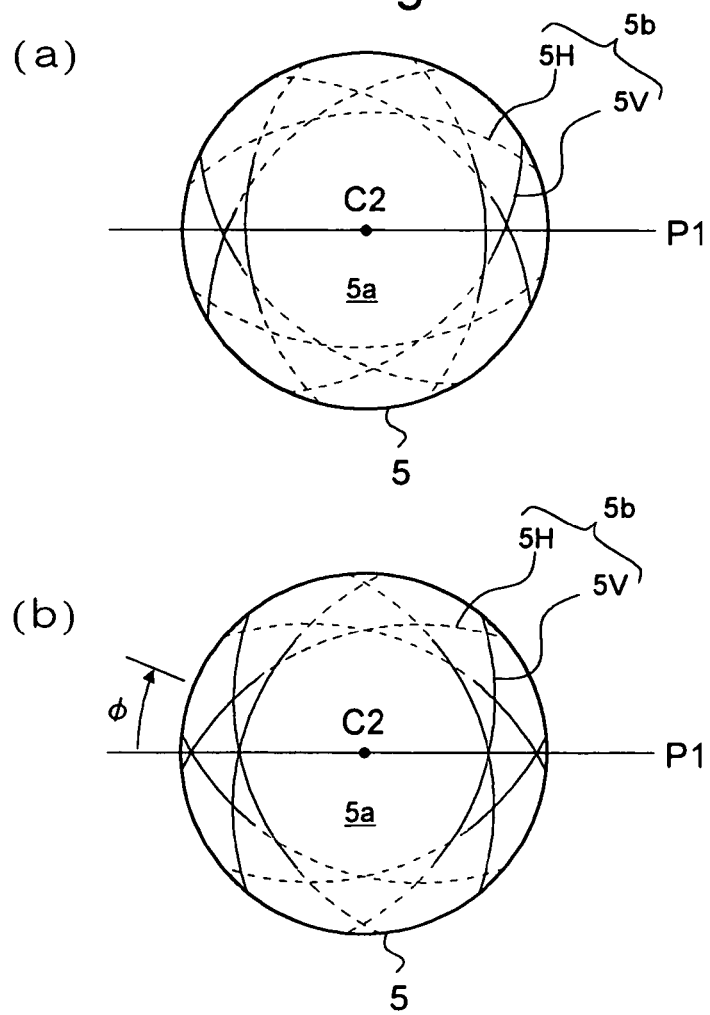
FIGS. 5-(a), 5(b) are schematic diagram describing a high intensity portion 5V and a low intensity portion 5H of scattered light in arc-shaped flaws.

The diffracted light that is emitted from the repetitive patterns on the surface under inspection 5a can be shut out by the polarization unit 22 because when linearly polarized light as illumination light for inspection is diffracted by the repetitive patterns on the surface under inspection 5a, the plane of vibration of the diffracted light is not rotated. In other words, the diffracted light from the repetitive patterns on the surface under inspection 5a is linearly polarized light. The plane of vibration of the diffracted light is in parallel with the plane of vibration of the linearly polarized light as illumination light for inspection. As shown in FIG. 4, when the orientations of the repetitive patterns are in parallel with or perpendicular to the plane of incidence P1, the plane of vibration of the diffracted light is precisely in parallel with the plane of vibration on the illumination side.

Thus, even if the diffracted light from the repetitive patterns on the surface under inspection 5a passes in the light reception range of the aperture angle δθr around the optical axis C4 of the light reception unit 20, it cannot pass through the polarization unit 22 disposed according to Crossed Nichols relative to the polarization unit 13 on the light illumination side. The polarization unit 22 shuts out the diffracted light. Thus, the diffracted light does not enter the light reception plane of the CCD image sensor 24. In other words, the diffracted light can be securely removed.

In contrast, when the linearly polarized light as illumination light for inspection is scattered by a foreign matter or a flaw (surface defect) on the surface under inspection 5a, the plane of vibration of the linearly polarized light is rotated. Diffracted light that is emitted from a surface defect contains a polarized light component perpendicular to the plane of vibration of the linearly polarized light as illumination light for inspection. Only the polarized light component passes through the polarization unit 22. The polarized light component is collected by the light reception lenses 21 and 23 and entered into the light reception plane of the CCD image sensor 24.

Thus, in the surface defect inspection apparatus 100 according to the first embodiment, since the light reception unit 20 is a dirk field optical system for specular light and the illumination unit 10 and the light reception unit 20 are provided with the polarization units 13 and 22, respectively, noise light (specular light, diffracted light, and so forth) not needed for an inspection for a surface defect on the surface under inspection 5a can be securely removed. Only scattered light emitted from a foreign matter, a flaw, or the like (surface defect) on the surface under inspection 5a can be entered into the light reception plane of the CCD image sensor 24.

Thus, the CCD image sensor 24 captures an image of the whole surface under inspection 5a with scattered light emitted from a foreign matter, a flaw, or the like (surface defect) of the surface under inspection 5a. Image information captured by the CCD image sensor 24 is output to the display unit 31 and the image processing unit 32.

The display unit 31 is made up of a CRT monitor, a liquid crystal display, or the like. The display unit 31 displays image information (an image of a surface defect) that is supplied from the CCD image sensor 24. The inspector can determine whether there is a surface defect on the object to be inspected 5 with the image on the display unit 31.

The image processing unit 32 performs an image processing for the image information that is supplied from the CCD image sensor 24 and determines that a portion of the captured image that exceeds a predetermined luminance have a surface defect such as a foreign matter or a flaw. Thus, it can be automatically inspected for a surface defect on the object to be inspected 5.

In the surface defect inspection apparatus 100 according to the first embodiment, since the illumination unit 10 and the light reception unit 20 are provided with the polarization units 13 and 22 that remove diffracted light that is emitted from the surface under inspection 5a, even if the optical axis of the diffracted light overlaps with the optical axis C4 of the light reception unit 20, the diffracted light can be securely removed and only scattered light that is emitted from a surface defect can be selected. As a result, an SN ratio necessary to perform an inspection for a surface defect can be securely obtained.

In particular, when there are many repetitive patterns having different pitches each, since diffracted light that is emitted from the repetitive patterns occur in various directions, it is difficult to adjust the angle conditions in the conventional manner and set the optical axis C4 and the aperture angle δθr of the light reception unit 20 so that diffracted light does not enter the surface under inspection 5a. However, when the polarization units 13 and 22 are used as with the first embodiment, even if there are many repetitive patterns having different pitches each, diffracted light can be securely removed. As a result, an SN ratio necessary to perform an inspection for a surface defect can be securely obtained.

In the surface defect inspection apparatus 100 according to the first embodiment, the incident angle θi of the optical axis C1 of the illumination unit 10 is set so that it satisfies the conditional expression (4) (namely, the output angle θo of specular light satisfies the conditional expression (5)). Thus, illumination light for inspection (linearly polarized light) can be downwardly entered to the surface under inspection 5a at a relatively small angle. As a result, a concave-shaped flaw on the surface under inspection 5a can securely generate scattered light. Thus, an SN ratio necessary to perform an inspection for a concave-shaped flaw can be securely obtained.

In the surface defect inspection apparatus 100 according to the first embodiment, since an SN ratio necessary to perform an inspection for a foreign matter such as dust or rubbish that adheres on the surface under inspection 5a or a convex- or concave-shaped flaw thereon can be securely obtained, the inspection for a surface defect can be properly performed.

In the surface defect inspection apparatus 100 according to the first embodiment, the illumination unit 10 illuminates the whole surface under inspection 5a and the CCD image sensor 24 of the light reception unit 20 captures an image of the whole surface under inspection 5a. Thus, since an inspection for a surface defect can be performed in a short time period, the throughput is improved.

In the surface defect inspection apparatus 100 according to the first embodiment, the illumination unit 10 and the light reception unit 20 each have a telecentric structure that faces the surface under inspection 5a. Thus, the illumination conditions of the illumination unit 10 and the light reception conditions of the light reception unit 20 can be constant over the whole surface under inspection 5a. As a result, an inspection for a surface defect can be more properly performed.

For an inspection for many arc-shaped flaws 5b (see FIG. 2) that have occurred due to the CMP treatment, scattered light from a portion 5V (FIG. 5(a)) substantially perpendicular to the plane of incidence P1 of each of the flaws 5b has sufficient intensity, but scattered light from a portion 5H substantially in parallel with the plane of incidence P1 is weak. Thus, even if the light reception unit 20 captures one image of a surface defect, it is not possible to inspect the flaws 5b entirely. A conceivable reason of the weak scattered light from the portion SH substantially in parallel with the plane of incidence P1 is that the surface under inspection 5a is illuminated with substantially collimated illumination light for inspection which is inclined to the normal line C2, and the ratio of specular light to scattered light on the inner wall surface of the flaws 5b is large.

In this case, the surface defect inspection apparatus 100 according to the first embodiment changes the illumination conditions (namely, the illumination direction to the surface under inspection 5a) of the illumination light for inspection by rotating the support table 1 around the axis AX1 according to an instruction from the control section 33. FIG. 5(b) shows a state that the surface under inspection 5a is rotated from the state shown in FIG. 5(a) only by an angle φ. As is clear from the comparison of FIG. 5(a) and FIG. 5(b), in a different illumination condition of the illumination light, the position of the portion 5V of the arc-shaped flaws 5b to maintain sufficient intensity of the scattered light is also varied.

While the support table 1 is being rotated, images of a surface defect are repeatedly captured by the light reception unit 20 in a plurality of different illumination conditions (FIG. 5(a) and FIG. 5(b)). In these captured images, the portion SV substantially perpendicular to the plane of incidence P1 corresponding to the illumination conditions appears as a bright image. The image information is also output to the display unit 31 and the image processing unit 32.

It is preferred that the support table 1 be rotated at equal intervals of predetermined angles in an angular range of 180 degrees or 360 degrees around the axis AX1. When the sectional shapes of the flaws 5b are symmetrical, it is preferred that the angular range be 180 degrees. When the sectional shapes of the flaws 5b are asymmetrical, it is preferred that the angular range be 360 degrees. The intervals of the rotation angles can be set according to the flaws 5b. When the support table 1 is rotated at intervals of 15 degrees, images can be captured in the conditions in which the illumination direction of the illumination light is changed at intervals of 15 degrees.

When the support table 1 is rotated at intervals of 15 degrees, if the angular range is 180 degrees, 12 images are captured; if the angular range is 360 degrees, 24 images are captured. Information with respect to these images is stored in a memory of the image processing unit 32 until the light reception unit 20 has completed the image capture operation.

When the image capture operation is completed, the image processing unit 32 combines the plurality of images that differ in illumination conditions of the illumination light and generates a combined image. At is point, taking account of the rotation angle of the support table 1 (namely, the rotation angle of the surface under inspection 5a), the images are combined so that individual positions of the surface under inspection 5a are matched in all the images. As shown in FIG. 2, in the combined image, the whole arc-shaped flaws 5b appear as a bright image.

Thereafter, the image processing unit 32 processes the generated combined image and determines that there is a surface defect such as the arc-shaped flaws 5b in a portion whose intensity exceeds predetermined intensity. Thus, even if there are arc-shaped flaws 5b on the surface under inspection 5a and a part of the flaws 5b is substantially in parallel with the plane of incidence P1, an inspection for the whole flaws 5b (their sizes and regions) can be properly performed. The combined image generated by the image processing unit 32 may be displayed on the display unit 31 so that an inspection can be visually performed. However, with the image processing unit 32, an inspection for a surface defect can be automatically and effectively performed.

As well as for the arc-shaped flaws 5b that occurred in the CMP treatment, the same inspection can be performed for concave-shaped flaws. This inspection is especially effective when the depth of flaws is shallow. When concave-shaped flaws are curved, by generating a combined image in the foregoing manner, an inspection for the whole flaws can be properly performed. When concave-shaped flaws are linear, an inspection for the flaws cannot be performed only in a particular illumination condition (of which the flaws are substantially in parallel with the plane of incidence P1). However, when a combined image is generated in the foregoing manner, images of which flaws are substantially perpendicular to the plane of incidence P1 can be used to perform an inspection for the linearly concave-shaped flaws. Thus, the inspection for these flaws can be properly performed. When there are flaws in various directions on the surface under inspection 5a, the inspection for the whole flaws can be properly performed.

When the support table 1 (object to be inspected 5) is rotated to generate a combined image, the angles of the orientations of the repetitive patterns on the surface under inspection 5a (FIG. 4) to the plane of incidence P1 change. Depending on the angles to the plane of incidence P1, diffracted light that is emitted from the repetitive patterns may not be properly removed. Angles at which diffracted light enters the light reception plane of the CCD image sensor 24 can be experimentally obtained with test wafers or the like in advance.

Thus, while the support table 1 (object to be inspected 5) is being rotated, when images are captured, it is preferred that images of which diffracted light enters the light reception plane of the CCD image sensor 24 be omitted and images of which diffracted light does not enter the light reception plane of the CCD image sensor 24 be captured. In this case, since all the images are captured in the state that diffracted light does not enter the light reception plane of the CCD image sensor 24, a combined image can be generated by all the captured images. Instead, images may be captured at many angles including those at which diffracted light enters the light reception plane of the CCD image sensor 24. In this case, images having high intensity of diffracted light may be removed from these captured images and the remaining images may be combined.

The inventors of the present invention have found that on various semiconductor wafers (object to be inspected 5) can be properly inspected for surface defects by the apparatus that is set in the state that θo of specular light is around 21 degrees, the angle θr of the optical axis C4 of the light reception unit 20 is around 2 degrees, the aperture angle δθo is around 0.6 degrees, and the aperture angle δθr is around 0.15 degrees and by the apparatus that is set in the state that θo is around 16 degrees, the angle θr is around 2 degrees, the aperture angle δθo is around 0.5 degrees, and the aperture angle δθr is around 0.15 degrees.

In addition, the inventors of the present invention have found through experiment that when a sample wafer is placed as an object to be inspected 5 on the support table 1 and while the support table 1 is being rotated around the axis AX1 at intervals of 22.5 degrees, nine images are captured and six images except for three images of which diffracted light that is emitted from repetitive patterns enters the CCD image sensor 24 are combined, an inspection for arc-shaped flaws 5b (FIG. 2) that occurred in the CMP treatment can be properly performed.

In addition, the inventors of the present invention have found through experiment that a good condition for an effective inspection for a surface defect with less diffracted light from repetitive pattern is to combine six images captured while the support table 1 is being rotated at intervals of 30 degrees. However, it should be noted that the intervals of angles at which the support table 1 (object to be inspected 5) is rotated and the number of images captured are not limited to the foregoing values. Since the intervals of angles at which the support table 1 is rotated and the number of images captured depend on the state of flaws on the surface under inspection 5*a*, they can be set according to the object to be inspected 5.

Second Embodiment

Figure 6:
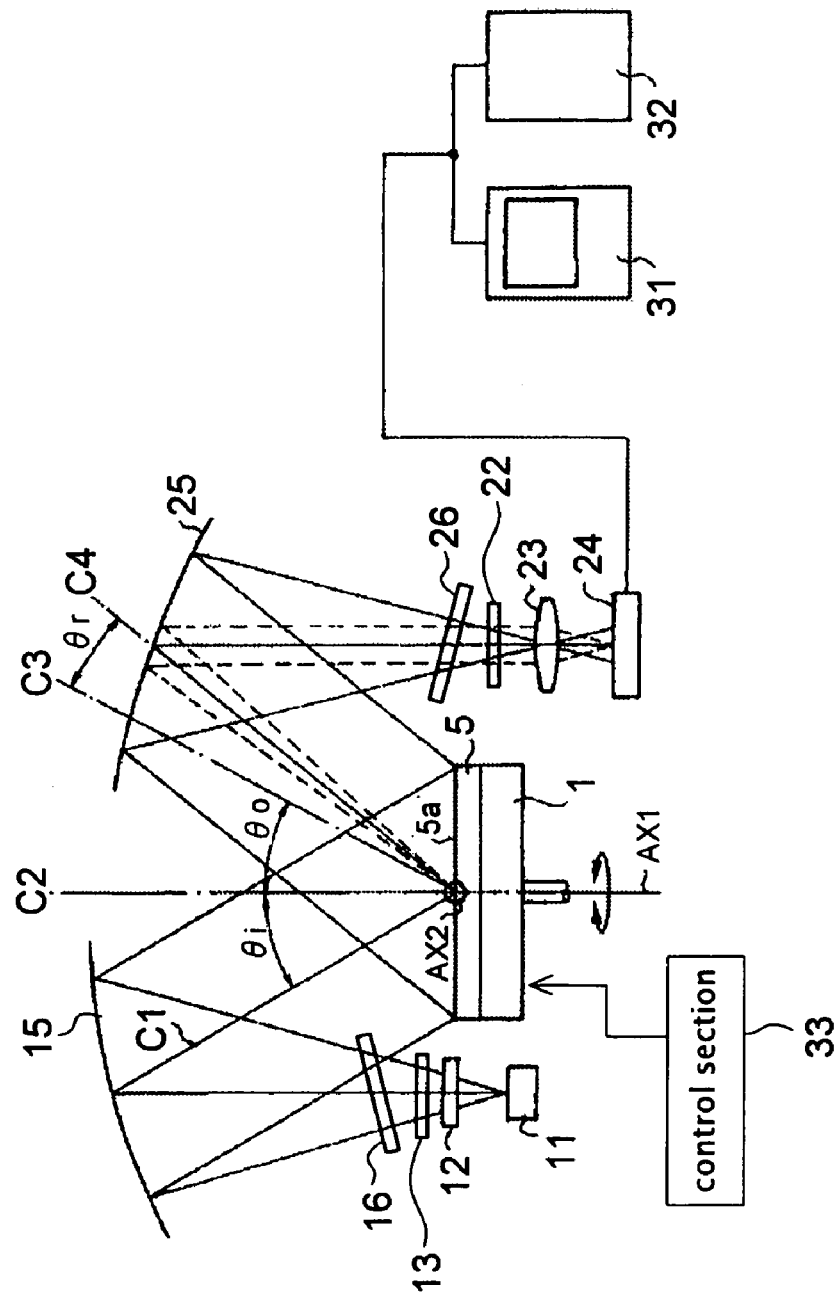
FIG. 6 is a schematic diagram showing a structure of a surface defect inspection apparatus 200 according to a second embodiment.

Next, with reference to FIG. 6, a second embodiment of the present invention will be described. As shown in FIG. 6, a surface defect inspection apparatus 200 according to the second embodiment includes spherical reflection mirrors 15 and 25 instead of the illumination lens 14 and the light reception lens 21 of the surface defect inspection apparatus 100 according to the first embodiment (FIG. 1). Polarization compensation plates 16 and 26 are diagonally inserted into optical paths between the spherical reflection mirrors 15 and 25 and the polarization units 13 and 22, respectively.

The polarization compensation plates 16 and 26 are plane-parallel plates made of glass having a high refractive index. It is preferred that the polarization compensation plates 16 and 26 be made of a material having a refractive index of 1.8 or greater (for example, around 1.9). The higher the refractive index, the better characteristics the polarization compensation plates 16 and 26 have. However, the optimal refractive index depends on the wavelength of light. For example, when ultraviolet light is used, it is preferred that the refractive index of the polarization compensation plates 16 and 26 be around 1.8, taking account of their transmissivity.

Likewise, in the surface defect inspection apparatus 200 according to the second embodiment, each unit is set so that the foregoing conditional expressions (4) to (7) are satisfied. A light reception unit (22 to 26) is a dirk field optical system relative to specular light. In addition, an illumination unit (11 to 13, 15, and 16) and the light reception unit (22 to 26) are provided with the polarization units 13 and 22, respectively. Thus, noise light (specular light, diffracted light, and so forth) that are not necessary to perform an inspection for a surface defect on the surface under inspection 5*a* can be securely removed.

Since the polarization units 13 and 22 remove diffracted light that is emitted from the surface under inspection 5*a*, even if an optical axis of the diffracted light overlaps with an optical axis C4 of the light reception unit (22 to 26), the diffracted light can be securely removed and only scattered light that is emitted from a surface defect can be selected. As a result, an SN ratio necessary to perform an inspection for a surface defect can be securely obtained. Even if there is a concave-shaped flaw on the surface under inspection 5*a*, scattered light can be securely generated therefrom. As a result, an SN ratio necessary to perform an inspection for a concave-shaped flaw can be securely obtained. Thus, the inspection for the surface defect can be properly performed.

Moreover, in the surface defect inspection apparatus 200 according to the second embodiment, since the polarization compensation plates 16 and 26 are disposed between the spherical reflection mirrors 15 and 25 and the polarization units 13 and 22, respectively, the extinction ratio on the whole surface under inspection 5*a* can be nearly constant. It is preferred that the front surfaces of the polarization compensation plates 16 and 26 be coated with a protection film having the similar refractive index as that of a glass material to prevent the polarization compensation plates 16 and 26 from becoming tarnish.

Moreover, in the surface defect inspection apparatus 200 according to the second embodiment, while the support table 1 (object to be inspected 5) is being rotated, a plurality of images are captured and they are combined. Thus, even if there is a concave-shaped flaw (or a part thereof) substantially in parallel with the plane of incidence P1, an inspection for the flaw can be properly performed.

Third Embodiment

Next, with reference to FIG. 7, a third embodiment of the present invention will be described.

Figure 7:
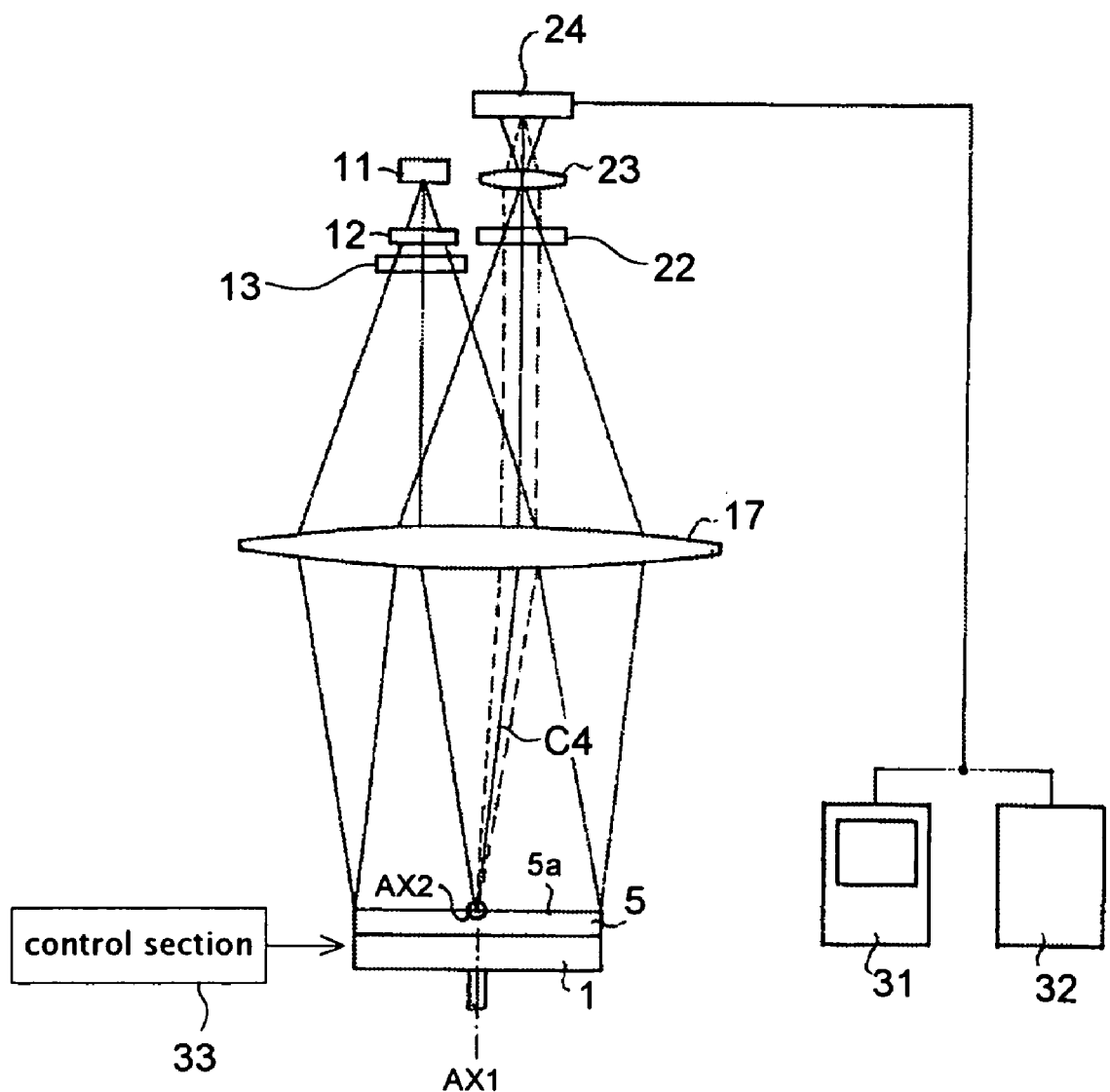
FIG. 7 is a schematic diagram showing a structure of a surface defect inspection apparatus 300 according to a third embodiment.

As shown in FIG. 7, a surface defect inspection apparatus 300 according to the third embodiment includes a large diameter lens 17 instead of the illumination lens 14 and the light reception lens 21 of the surface defect inspection apparatus 100 (FIG. 1) according to the first embodiment.

In the surface defect inspection apparatus 300 according to the third embodiment, an illumination unit (11 to 13 and 17) and a light reception unit (17 and 22 to 24) share the large diameter lens 17. Thus, the structure of the apparatus 300 is simplified. However, the illumination unit (11 to 13 and 17) and the light reception unit (17 and 22 to 24) need to be closely disposed. As a result, an incident angle θi of illumination light for inspection and an output angle θo of specular light become small.

Likewise, in the surface defect inspection apparatus 300 according to the third embodiment, each unit is set so that the foregoing conditional expressions (4) to (7) are satisfied. The light reception unit (17 and 22 to 24) is a dirk field optical system relative to specular light and the illumination unit (11 to 13 and 17) and the light reception unit (17 and 22 to 24) are provided with polarization units 13 and 22, respectively. Thus, noise light (specular light, diffracted light, and so forth) that are not necessary to perform an inspection for a surface defect on the surface under inspection 5*a* can be securely removed.

In addition, since the polarization units 13 and 22 remove diffracted light that is emitted from the surface under inspection 5*a*, even if an optical axis of the diffracted light overlaps with an optical axis C4 of the light reception unit (17 and 22 to 24), the diffracted light can be securely removed and only scattered light that is emitted from a surface defect can be selected. As a result, an SN ratio necessary to perform an inspection for a surface defect can be securely obtained. In addition, even if there is a concave-shaped flaw on the surface under inspection 5*a*, scattered light can be securely generated therefrom. As a result, an SN ratio necessary to perform an inspection for a concave-shaped flaw can be securely obtained. Thus, the inspection for the surface defect can be properly performed.

Moreover, in the surface defect inspection apparatus 300 according to the third embodiment, while the support table 1 (object to be inspected 5) is being rotated, a plurality of images are captured and they are combined. Thus, even if there is a concave-shaped flaw (or a part thereof) substantially in parallel with the plane of incidence P1, an inspection for the flaw can be properly performed.

Fourth Embodiment

Next, with respect to FIG. 8, a fourth embodiment of the present invention will be described.

As shown in FIG. 8, a surface defect inspection apparatus 400 according to the fourth embodiment includes a concave-shaped surface reflection mirror 18 instead of the large diameter lens 17 according to the third embodiment. In addition, polarization compensation plates 16 and 26 that are the same as those according to the second embodiment are diagonally inserted into optical paths between the concave-shaped surface reflection mirror 18 and the polarization units 13 and 22, respectively, In the surface defect inspection apparatus 400 according to the fourth embodiment, an illumination unit (11 to 13, 16, and 18) and a light reception unit (18, 22 to 24, and 26) share the concave-shaped surface reflection mirror 18. Thus, the structure of the apparatus is simplified. In addition, the surface defect inspection apparatus 400 becomes compact in size in comparison with the apparatus including the lens 17 according to the third embodiment.

Likewise, in the surface defect inspection apparatus 400 according to the fourth embodiment, each unit is set so that the foregoing conditional expressions (4) to (7) are satisfied. The light reception unit (18, 22 to 24, and 26) is a dirk field optical system relative to specular light and the illumination unit (11 to 13, 16, and 18) and the light reception unit (18, 22 to 24, and 26) are provided with polarization units 13 and 22, respectively. Thus, noise light (specular light, diffracted light, and so forth) that are not necessary to perform an inspection for a surface defect on the surface under inspection 5a can be securely removed.

In addition, since the polarization units 13 and 22 remove diffracted light that is emitted from the surface under inspection 5a, even if an optical axis of the diffracted light overlaps with an optical axis C4 of the light reception unit (18, 22 to 24, and 26), the diffracted light can be securely removed and only scattered light that is emitted from a surface defect can be selected. As a result, an SN ratio necessary to perform an inspection for a surface defect can be securely obtained. In addition, even if there is a concave-shaped flaw on the surface under inspection 5a, scattered light can be securely generated therefrom. As a result, an SN ratio necessary to perform an inspection for a concave-shaped flaw can be securely obtained. Thus, the inspection for the surface defect can be properly performed.

Moreover, in the surface defect inspection apparatus 400 according to the fourth embodiment, while the support table 1 (object to be inspected 5) is being rotated, a plurality of images are captured and they are combined. Thus, even if there is a concave-shaped flaw (or a part thereof) substantially in parallel with the plane of incidence P1, an inspection for the flaw can be properly performed.

(Modifications of First to Fourth Embodiments)

In the foregoing embodiments, an example of which the optical axis C4 of the light reception unit 20 is contained in the plane of incidence P1 (formed of the optical axis C1 of the illumination unit and the normal line C2 of the surface under inspection 5a) was described. However, it should be noted that the present invention is not limited to such an example. For instance, as shown in FIG. 9(a) viewed from arrow III in FIG. 1 and FIG. 3, a plane P2 containing the optical axis C3 of specular light and the optical axis C4 of the light reception unit 20 may be inclined to the plane of incidence P1 at a predetermined angle θs. In this case, the angle θr of the optical axis C4 of the light reception unit 20 is set so that the conditional expressions (6) and (7) are satisfied on the plane P2.

Instead, as shown in FIG. 9(b) viewed from arrow III in FIG. 1 and FIG. 3, the plane P3 containing the optical axis C3 of specular light and the optical axis C4 of the light reception unit 20 may have an angle θs=90 degrees relative to the plane of incidence P1. In this case, while the angle θr of the optical axis C4 is kept constant, the incident angle θi of the optical axis C1 of the illumination unit and the output angle θo of the optical axis C3 of specular light can be easily changed.

As shown in FIG. 9(a) and FIG. 9(b), when the planes P2 and P3 containing the optical axis C3 of specular light and the optical axis C4 of the light reception unit 20 are inclined to the plane of incidence P1, the angle θr of the optical axis C4 can be set by rotating (shaking) the light reception unit 20 itself around the axis AX3. The axis AX3 is an axis that passes through the intersection of the optical axis C1 of the illumination unit 10 and the surface under inspection 5a and that is perpendicular to the planes P2 and P3.

According to the foregoing embodiments, the polarization units 13 and 22 are fixedly disposed in predetermined optical paths. Instead, the polarization units 13 and 22 may be detachably disposed in the optical paths. When an inspection for flaws 5b (FIG. 2) that occurred in the CMP treatment for the surface under inspection 5a on which repetitive patterns are fully formed is performed and scattered light that is emitted from the flaws 5b is received, linearly polarized light is used to improve the SN ratio. In this case, it is preferred that the polarization units 13 and 22 be inserted into the optical paths. Otherwise, it is preferred that the polarization units 13 and 22 be removed from the optical paths.

According to the foregoing embodiments, an example of which the polarization units 13 and 22 remove diffracted light that is emitted from the surface under inspection 5a was described. In addition to the polarization units 13 and 22 (or instead thereof), angle conditions may be adjusted in the following manner. The angle θr of the optical axis C4 of the light reception unit 20 is set to the smallest angle (that is close to the optical axis C3 of specular light) in an angle range that allows a dirk field optical system to be structured relative to specular light . In addition, the angle θr is set to an angle that allows a dirk field optical system to be structured relative to diffused light. These angular adjustments allow diffracted light to be more securely removed.

The output direction of diffracted light depends on pitches of repetitive patterns formed on the surface under inspection 5a and the wavelength of illumination light. Thus, by changing the wavelength of the illumination light, diffracted light can be prevented from being guided to the light reception unit 20. In this case, however, the same wavelength of the illumination light is selectively set by the wavelength selection unit 12 of the illumination unit 10 and the diffraction angle is adjusted so that diffracted light is not guided to the light reception unit 20. In this case, the wavelength selection unit may be disposed in the light reception unit so that the light reception side can select the wavelength of the diffracted light.

In the foregoing embodiments, an example of which the polarization units 13 and 22 are provided and the angle conditions are adjusted to remove diffracted light was described. However, the present invention is not limited to such an example. When the intensity of diffracted light that is emitted from flaws on the surface under inspection 5a is sufficiently larger than the intensity of diffracted light that is emitted from the repetitive pattern, it may not be necessary to remove the diffracted light. In other words, an SN ratio of scattered light necessary to perform an inspection for a surface defect can be securely obtained without need to remove the diffracted light. Thus, flaws can be easily detected.

In the foregoing embodiments, to change the illumination conditions for the surface under inspection 5a, the support table 1 (object to be inspected 5) is rotated around the axis AX1. However, the present invention is not limited to these embodiments. Instead of rotating the support table 1, the illumination unit 10 may be rotated around the axis AX1. Instead, both the support table 1 and the illumination unit 10 may be rotated. In other words, when the object to be inspected 5 and the illumination unit 10 are relatively rotated around each other, the illumination conditions for the surface under inspection 5a can be changed.

In the foregoing embodiments, an example of which the incident angle θi of the optical axis C1 of the illumination unit satisfies the conditional expression (4), the output angle θo of specular light satisfies the conditional expression (5), and the angle θr of the optical axis C4 of the light reception unit satisfies the conditional expression (6) was described. However, the present invention is not limited to such an example. Instead, when the incident angle θi and the output angle θo are greater than 60 degrees and/or the angle θr of the optical axis C4 is greater than 10 degrees, the present invention can be applied.

Fifth Embodiment

Next, with reference to FIG. 10, a fifth embodiment of the present invention will be described in detail.

Figure 10:
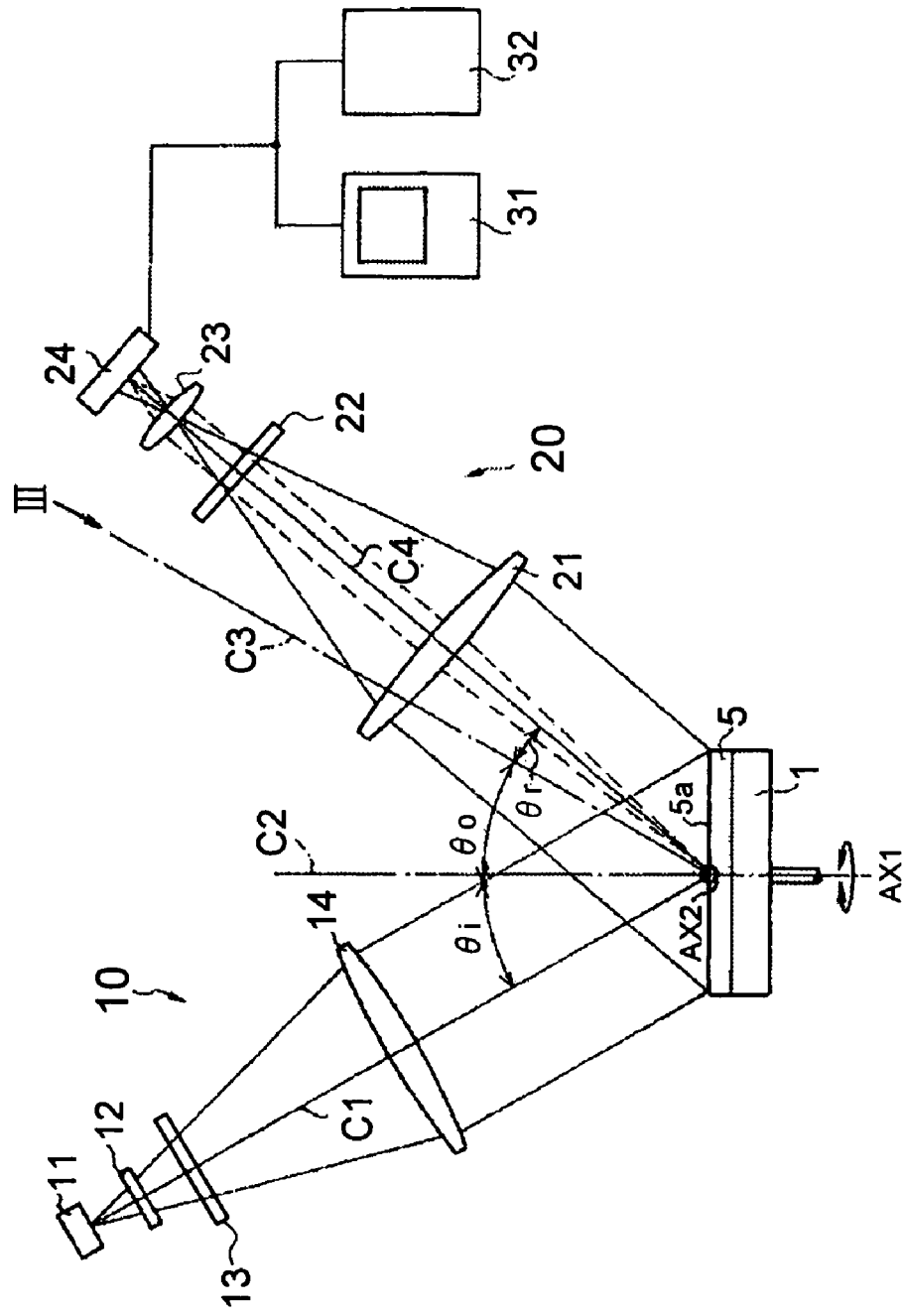
FIG. 10 is a schematic diagram showing a structure of a surface defect inspection apparatus 100 according to a fifth embodiment.

As shown in FIG. 10, a surface defect inspection apparatus 100 according to the fifth embodiment is made up of a support table 1 that supports an object to be inspected 5 such as a semiconductor wafer, an illumination unit 10 that illuminates the front surface of the object to be inspected 5 (hereinafter, referred to as "the surface under inspection 5a") with illumination light for inspection, a light reception unit 20 that receives scattered light that is emitted from the surface under inspection 5a, a display unit 31 and an image processing unit 32 that are connected to the light reception unit 20. The support table 1, the illumination unit 10, and the light reception unit 20 are disposed in a chamber (not shown).

The surface defect inspection apparatus 100 is a device that performs an inspection for a surface defect on the object to be inspected 5 in a fabrication process for an IC chip, a liquid crystal display panel, or the like.

In the surface defect inspection apparatus 100 according to the fifth embodiment, to securely remove noise light that is emitted from the surface under inspection 5a and effectively guide scattered light to the light reception unit 20, angle conditions of an optical axis C1 of the illumination unit 10 and an optical axis C4 of the light reception unit 20 are adjusted and polarization units 13 and 22 are disposed in the illumination unit 10 and the light reception unit 20, respectively.

Next, the structure of the surface defect inspection apparatus 100 according to the fifth embodiment will be specifically described.

The support table 1 can be rotated on a horizontal plane around an axis AX1 that passes through the center of the surface under inspection 5a and extends in the vertical direction. The support table 1 is rotated around the axis AX1 when the orientations (for example, repetitive directions) of repetitive patterns formed on the surface under inspection 5a are adjusted. The orientations of the repetitive patterns are adjusted so that they are in parallel with or perpendicular to a plane of the optical axis C1 of the illumination unit 10 and a normal line C2 of the surface under inspection 5a (this plane is hereinafter referred to as "the plane of incidence P1") as shown in FIG. 4. Instead, the orientations of the repetitive patterns may have an angle relative to the plane of incidence P1.

In addition, the support table 1 can be rotated (shaken) around an axis AX2 that extends in the horizontal direction. The axis AX2 passes through the intersection of the optical axis C1 of the illumination unit 10 and the surface under inspection 5a and is perpendicular to the plane of incidence P1 (formed of the optical axis C1 and a normal line C2 of the surface under inspection 5a). When the angle conditions of the optical axis C1 of the illumination unit 10 and so forth are adjusted, the support table 1 is rotated around the axis AX2.

The illumination unit 10 is made up of a light source 11, a wavelength selection unit 12, a polarization unit 13, and an illumination lens 14. The optical axis C1 of the illumination unit 10 is inclined to the normal line C2 of the surface under inspection 5a. The angle between the optical axis C1 and the normal line C2, namely incident angle θi, is set so that the following conditional expression (4) is satisfied.

$$\theta i \leq 60 \text{ degrees} \tag{4}$$

The incident angle θi of the optical axis C1 of the illumination unit 10 can be set by rotating (shaking) the support table 1 around the axis AX2. Instead, the incident angle θi of the optical axis C1 of the illumination unit 10 may be set by rotating (shaking) the illumination unit 10 around the axis AX2 instead of the rotation of the support table 1 (or in addition to the rotation of the support table 1).

Examples of the light source 11 include a metal halide lamp, a mercury lamp, and a halogen lamp. The wavelength selection unit 12 selects a wavelength by changing various types of dichroic mirrors or interference mirrors. The wavelength selection unit 12 selectively allows light having a predetermined wavelength of light emitted from the light source 11 to pass.

Examples of the polarization unit 13 include a sheet film type polarization plate and a liquid crystal device. The polarization unit 13 converts light that is supplied from the wavelength selection unit 12 into linearly polarized light. The illumination lens 14 converts the linearly polarized light that is supplied from the polarization unit 13 into collimated light. The whole surface under inspection 5a is illuminated with the collimated light as the illumination light for inspection. The illumination unit 10 has a telecentric structure that faces the surface under inspection 5a.

Thus, the whole surface under inspection 5a is illuminated with the linearly polarized light (illumination light for inspection) emitted from the illumination unit 10. The direction of the plane of vibration of the linearly polarized light is set in parallel with or perpendicular to the plane of incidence P1 by the polarization unit 13. Instead, the direction of the plane of vibration of the linearly polarized light may be inclined to the plane of incidence P1. The wavelength of the linearly polarized light is set by the wavelength selection unit 12. The incident angle of the linearly polarized light is equivalent to the incident angle θi of the optical axis C1 of the illumination unit 10. The incident angle of the linearly polarized light is constant on the whole surface under inspection 5a.

When the surface under inspection 5a is illuminated with the linearly polarized light, specular light is emitted therefrom in a direction of an optical axis C3 at an output angle θo. The output angle θo is an angle between the optical axis C3 of the specular light and the normal line C2 of the surface under inspection 5a. Thus, the output angle θo is equal to the incident angle θi of the linearly polarized light. As a result, when the incident angle θi satisfies the foregoing conditional expression (4), the output angle θo satisfies the following conditional expression (5).

$$\theta o \leq 60 \text{ degrees} \qquad (5)$$

The light reception unit 20 is made up of a first light reception lens 21, a polarization unit 22, a second light reception lens 23, and a CCD image sensor 24. The optical axis C4 of the light reception unit 20 is inclined to the optical axis C3 of the specular light. The angle between the optical axis C4 of the light reception unit 20 and the optical axis C3 (namely, an angle θr between the optical axis C3 and the optical axis C4) is set so that the following conditional expression (6) is satisfied.

$$\theta r \leq 10 \text{ degrees} \qquad (6)$$

The optical axis C4 of the light reception unit 20 is contained in the same plane of the optical axis C1 of the illumination unit 10 and the optical axis C3 of the specular light. This plane is equivalent to the plane of incidence P1 and is in parallel with the drawing of FIG. 10.

As shown in FIG. 3, even if the specular light spreads in a circular cone shape around the optical axis C3 at an aperture angle δθo, the angle θr and the optical axis C4 is set so that the aperture angle δθo does not overlap with an aperture angle δθr around the optical axis C4 of the light reception unit 20, namely the following conditional expression (7) is satisfied.

$$\delta\theta i \, o < (\theta r - \delta\theta r) \qquad (7)$$

When the conditional expression (7) is satisfied, the specular light that is emitted from the surface under inspection 5a does not enter the circularly-conical shape light reception range (aperture angel δθr) of the light reception unit 20. Thus, the light reception unit 20 becomes a dirk field optical system relative to the specular light. In other words, specular light as one component of noise light that is not necessary to perform an inspection for a surface defect on the surface under inspection 5a can be securely removed.

When the incident angle θi of the optical axis C1 of the illumination unit 10 is set, the output angle θo of the specular light can be automatically obtained. In other words, when at least one of the support table 1 and the illumination unit 10 is rotated (shaken) around the axis AX2, the incident angle θi and the output angle θo can be set. In addition, the angle θr and the optical axis C4 of the light reception unit 20 can be set by rotating (shaking) the light reception unit 20 around the axis AX2.

The light reception lenses 21 and 23 of the light reception unit 20 collect light (scattered light, specular light, diffracted light, and so forth) that is emitted from the surface under inspection 5a. Like the polarization unit 13, the polarization unit 22 is for example a polarization plate or a liquid crystal device. The polarization unit 22 passes a polarized light component perpendicular to the plane of vibration of the linearly polarized light as illumination light for inspection (namely, the polarization unit 22 shuts out a horizontally polarized light component). In other words, the polarization unit 22 is disposed according to so-called Crossed Nichols. The light reception unit 20 has a telecentric structure that faces the surface under inspection 5a. The CCD image sensor 24 can capture an image of the whole surface under inspection 5a.

Specular light that is emitted from the surface under inspection 5a is one component of noise light not needed for an inspection for a surface defect on the surface under inspection 5a. As described above, the specular light passes outside the light reception range of the aperture angle δθr around the optical axis C4 of the light reception unit 20 (namely, in the aperture angle δθo around the optical axis C3). Thus, even if the specular light is collected by the first light reception lenses 21 and 23, the specular light does not enter the light reception plane of the CCD image sensor 24. In other words, the specular light can be securely removed.

On the other hand, diffracted light that is emitted from repetitive patterns of the surface under inspection 5a is one component of noise light that is not necessary to perform an inspection for a surface defect on the surface under inspection 5a. However, normally, the output direction of the diffracted light is different from that of the specular light. In addition, depending on the pitches of the repetitive patterns, the angle between the optical axis C3 of the specular light and the optical axis of the diffracted light may get close to the angle θr of the optical axis C4 of the light reception unit 20. In this case, the diffracted light passes in the light reception range of the aperture angle δθr around the optical axis C4. Unless the polarization unit 22 is disposed, the diffracted light enters the light reception plane of the CCD image sensor 24.

However, since the surface defect inspection apparatus 100 according to the fifth embodiment is provided with the polarization unit 22, it passes a polarized light component perpendicular to the plane of vibration of the linearly polarized light as illumination light for inspection (namely, the polarization unit 22 shuts out a polarized light component in parallel with the plane of vibration). Thus, even if the diffracted light that is emitted from the repetitive patterns on the surface under inspection 5a passes in the light reception range of the aperture angle δθr around the optical axis C4 of the light reception unit 20, the polarization unit 22 shuts out the diffracted light so that it does not enter the light reception plane of the CCD image sensor 24.

The diffracted light that is emitted from the repetitive patterns on the surface under inspection 5a can be shut out by the polarization unit 22 because when linearly polarized light as illumination light for inspection is diffracted by the repetitive patterns on the surface under inspection 5a, the plane of vibration of the diffracted light is not rotated. In other words, the diffracted light that is emitted from the repetitive patterns on the surface under inspection 5a is linearly polarized light. The plane of vibration of the diffracted light is in parallel with the plane of vibration of the linearly polarized light as illumination light for inspection. As shown in FIG. 4, when the orientations of the repetitive patterns are in parallel with or perpendicular to the plane of incidence P1, the plane of vibration of the diffracted light is precisely in parallel with the plane of vibration on the illumination side.

Thus, even if the diffracted light that is emitted from the repetitive patterns on the surface under inspection 5a passes in the light reception range of the aperture angle δθr around the optical axis C4 of the light reception unit 20, the diffracted light cannot pass through the polarization unit 22 disposed according to Crossed Nichols relative to the polarization unit 13 on the light illumination side. The polarization unit 22 shuts out the diffracted light. Thus, the diffracted light does not enter the light reception plane of the CCD image sensor 24. In other words, the diffracted light can be securely removed.

In contrast, when the linearly polarized light as illumination light for inspection is scattered by a foreign matter or a flaw (surface defect) on the surface under inspection 5a, the plane of vibration of the linearly polarized light is rotated. Diffracted light that is emitted from the surface defect contains a polarized light component perpendicular to the plane of vibration of the linearly polarized light as illumination light for inspection. Only the polarized light component passes through the polarization unit 22. The polarized light component is collected by the light reception lenses 21 and 23 and entered into the light reception plane of the CCD image sensor 24.

Thus, in the surface defect inspection apparatus 100 according to the fifth embodiment, since the light reception unit 20 is a dirk field optical system for specular light and the illumination unit 10 and the light reception unit 20 are provided with the polarization units 13 and 22, respectively, noise light (specular light, diffracted light, and so forth) that is not necessary to perform an inspection for a surface defect on the surface under inspection 5a can be securely removed. Only scattered light emitted from a foreign matter, a flaw, or the like (surface defect) on the surface under inspection 5a can be entered into the light reception plane of the CCD image sensor 24.

Thus, the CCD image sensor 24 captures an image of the whole surface under inspection 5a with scattered light emitted from a foreign matter, a flaw, or the like (surface defect) of the surface under inspection 5a. Image information captured by the CCD image sensor 24 is output to the display unit 31 and the image processing unit 32.

The display unit 31 is made up of a CRT monitor, a liquid crystal display, or the like. The display unit 31 displays image information (an image of a surface defect) that is supplied from the CCD image sensor 24. The inspector can determine whether there is a surface defect on the object to be inspected 5 with the image on the display unit 31.

The image processing unit 32 performs an image process for the image information that is supplied from the CCD image sensor 24 and determines that a portion of the captured image that exceeds a predetermined luminance have a surface defect such as a foreign matter or a flaw. Thus, it can be automatically inspected for a surface defect on the object to be inspected 5.

In the surface defect inspection apparatus 100 according to the fifth embodiment, since the illumination unit 10 and the light reception unit 20 are provided with the polarization units 13 and 22 that remove diffracted light that is emitted from the surface under inspection 5a, even if the optical axis of the diffracted light overlaps with the optical axis C4 of the light reception unit 20, the diffracted light can be securely removed and only scattered light that is emitted from a surface defect can be selected. As a result, an SN ratio necessary to perform an inspection for a surface defect can be securely obtained.

In particular, when there are many repetitive patterns having different pitches each, since diffracted light that is emitted from the repetitive patterns occur in various directions, it is difficult to adjust the angle conditions in the conventional manner and set the optical axis C4 and the aperture angle δθr of the light reception unit 20 so that diffracted light does not enter the surface under inspection 5a. However, when the polarization units 13 and 22 are used as with the fifth embodiment, even if there are many repetitive patterns having different pitches each, diffracted light can be securely removed. As a result, an SN ratio necessary to perform an inspection for a surface defect can be securely obtained.

In the surface defect inspection apparatus 100 according to the fifth embodiment, the incident angle θi of the optical axis C1 of the illumination unit 10 is set so that it satisfies the conditional expression (4) (namely, the output angle θo of specular light satisfies the conditional expression (5)). Thus, illumination light for inspection (linearly polarized light) can be downwardly entered to the surface under inspection 5a at a relatively small angle. As a result, a concave-shaped flaw on the surface under inspection 5a can securely generate scattered light. Thus, an SN ratio necessary to perform an inspection for a concave-shaped flaw can be securely obtained.

In the surface defect inspection apparatus 100 according to the fifth embodiment, since an SN ratio necessary to perform an inspection for a foreign matter such as dust or rubbish that adheres on the surface under inspection 5a or a convex- or concave-shaped flaw thereon can be securely obtained, the inspection for a surface defect can be properly performed.

The inventors of the present invention have found that various semiconductor wafers (object to be inspected 5) can be properly inspected for surface defects by the apparatus that is set in the state that θo of specular light is around 21 degrees, the angle θr of the optical axis C4 of the light reception unit 20 is around 2 degrees, the aperture angle δθo is around 0.6 degrees, and the aperture angle δθr is around 0.15 degrees and by the apparatus that is set in the state that θo is around 16 degrees, the angle θr is around 2 degrees, the aperture angle δθo is around 0.5 degrees, and the aperture angle δθr is around 0.15 degrees.

In the surface defect inspection apparatus 100 according to the fifth embodiment, the illumination unit 10 illuminates the whole surface under inspection 5a and the CCD image sensor 24 of the light reception unit 20 captures an image of the whole surface under inspection 5a. Thus, since an inspection for a surface defect can be performed in a short time period, the throughput is improved.

In the surface defect inspection apparatus 100 according to the fifth embodiment, the illumination unit 10 and the light reception unit 20 each have a telecentric structure that faces the surface under inspection 5a. Thus, the illumination conditions of the illumination unit 10 and the light reception conditions of the light reception unit 20 can be constant over the whole surface under inspection 5a. As a result, an inspection for a surface defect can be more properly performed.

The foregoing effect can be obtained when the orientations of the repetitive patterns on the surface under inspection 5a have an angle to the plane of incidence P1 as well as the case that the repetitive patterns on the surface under inspection 5a are in parallel with or perpendicular to the plane of incidence P1. However, it is preferred that the repetitive patterns on the surface under inspection 5a be in parallel with or perpendicular to the plane of incidence P1 because the plane of vibration of linearly polarized light can be securely prevented from being varied.

Sixth Embodiment

Figure 11:
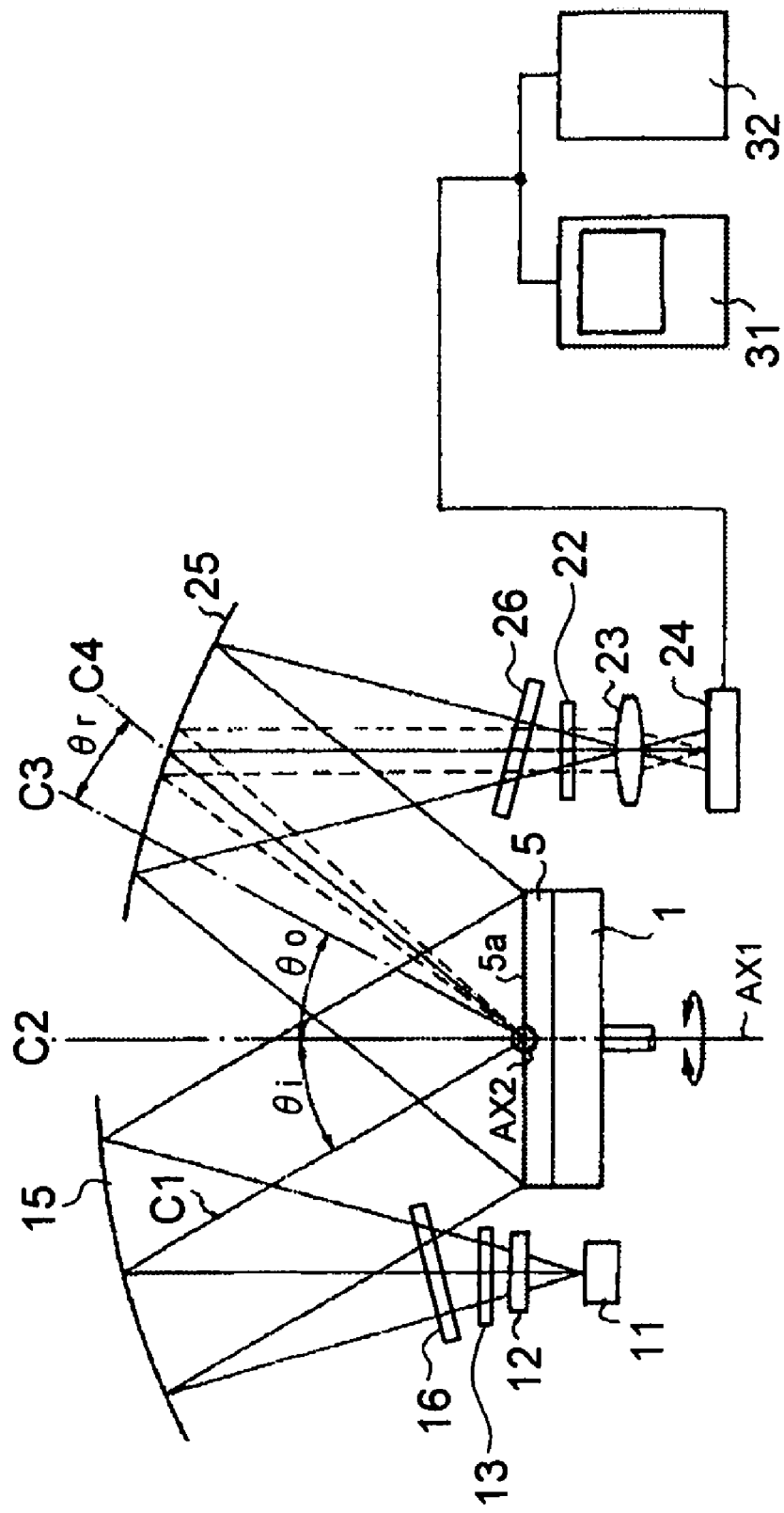
FIG. 11 is a schematic diagram showing a structure of a surface defect inspection apparatus 200 according to a sixth embodiment.

Next, with reference to FIG. 11, a sixth embodiment of the present invention will be described. As shown in FIG. 11, a surface defect inspection apparatus 200 according to the sixth embodiment includes spherical reflection mirrors 15 and 25 instead of the illumination lens 14 and the light reception lens 21 of the surface defect inspection apparatus 100 (FIG. 10) according to the fifth embodiment. Polarization compensation plates 16 and 26 are diagonally inserted into optical paths between the spherical reflection mirrors 15 and 25 and the polarization units 13 and 22, respectively.

The polarization compensation plates 16 and 26 are plane-parallel plates made of glass having a high refractive index. It is preferred that the polarization compensation plates 16 and 26 be made of a material having a refractive index of 1.8 or greater (for example, around 1.9). The higher the refractive index, the better characteristics the polarization compensation plates 16 and 26 have. However, the optimal refractive index depends on the wavelength of light. For example, when ultraviolet light is used, it is preferred that the refractive index of the polarization compensation plates 16 and 26 be around 1.8, taking account of their transmissivity.

Likewise, in the surface defect inspection apparatus 200 according to the sixth embodiment, each unit is set so that the foregoing conditional expressions (4) to (7) are satisfied. A light reception unit (22 to 26) is a dirk field optical system relative to specular light. In addition, an illumination unit (11 to 13, 15, and 16) and the light reception unit (22 to 26) are provided with the polarization units 13 and 22, respectively. Thus, noise light (specular light, diffracted light, and so forth) that are not necessary to perform an inspection for a surface defect on the surface under inspection 5a can be securely removed.

Since the polarization units 13 and 22 remove diffracted light that is emitted from the surface under inspection 5a, even if an optical axis of the diffracted light overlaps with an optical axis C4 of the light reception unit (22 to 26), the diffracted light can be securely removed and only scattered light that is emitted from a surface defect can be selected. As a result, an SN ratio necessary to perform an inspection for a surface defect can be securely obtained. Even if there is a concave-shaped flaw on the surface under inspection 5a, scattered light can be securely generated therefrom. As a result, an SN ratio necessary to perform an inspection for a concave-shaped flaw can be securely obtained. Thus, the inspection for the surface defect can be properly performed.

Moreover, in the surface defect inspection apparatus 200 according to the sixth embodiment, since the polarization compensation plates 16 and 26 are disposed between the spherical reflection mirrors 15 and 25 and the polarization units 13 and 22, respectively. Thus, the extinction ratio on the whole surface under inspection 5a can be nearly constant. It is preferred that the front surfaces of the polarization compensation plates 16 and 26 be coated with a protection film having the similar refractive index as that of a glass material to prevent the polarization compensation plates 16 and 26 from becoming tarnish.

Seventh Embodiment

Next, with reference to FIG. 12, a seventh embodiment of the present invention will be described.

Figure 12:
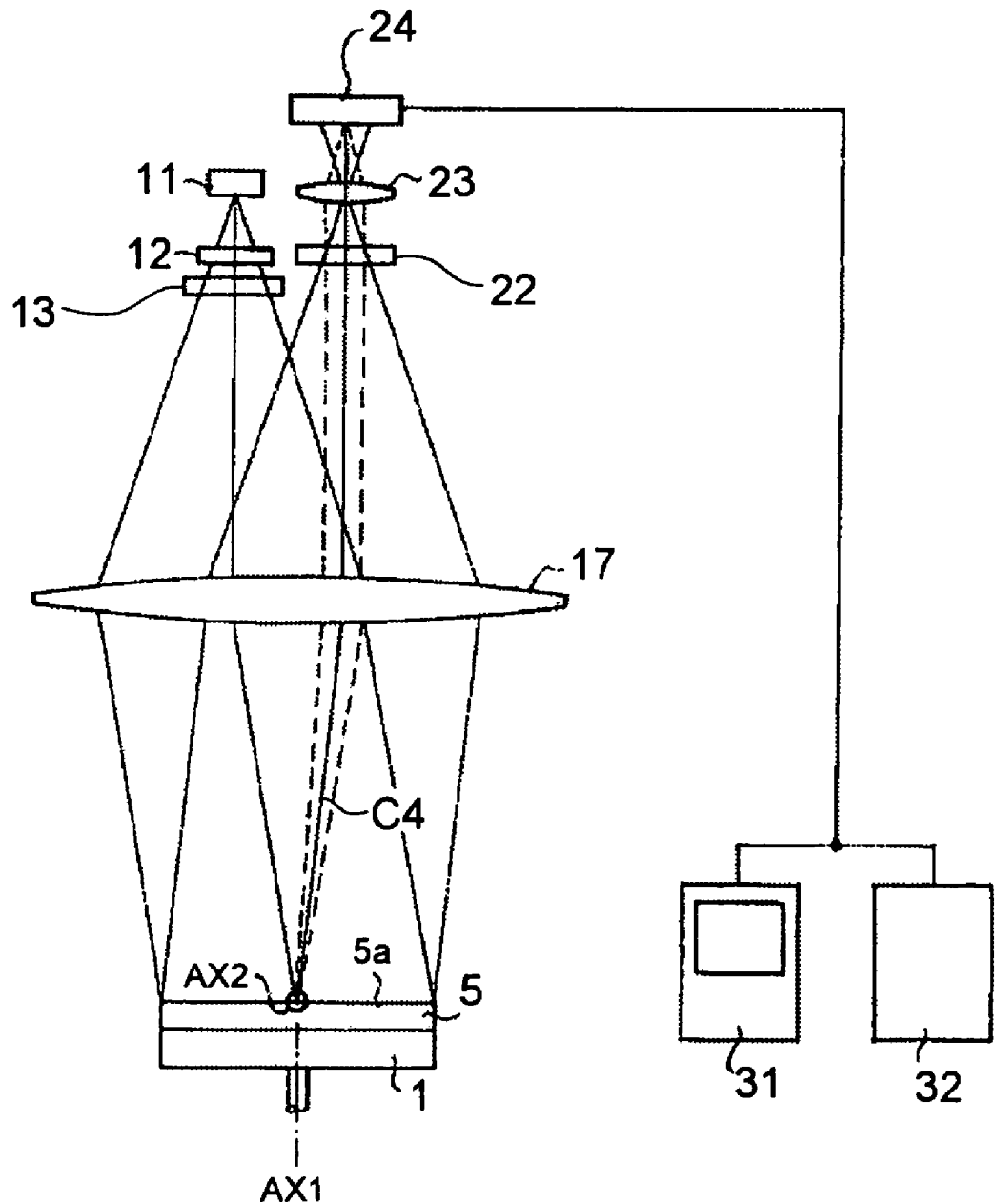
FIG. 12 is a schematic diagram showing a structure of a surface defect inspection apparatus 300 according to a seventh embodiment.

As shown in FIG. 12, a surface defect inspection apparatus 300 according to the seventh embodiment includes a large diameter lens 17 instead of the illumination lens 14 and the light reception lens 21 of the surface defect inspection apparatus 100 (FIG. 10) according to the fifth embodiment.

In the surface defect inspection apparatus 300 according to the seventh embodiment, an illumination unit (11 to 13 and 17) and a light reception unit (17 and 22 to 24) share the large diameter lens 17. Thus, the structure of the apparatus 300 is simplified. However, the illumination unit (11 to 13 and 17) and the light reception unit (17 and 22 to 24) need to be closely disposed. As a result, an incident angle θi of illumination light for inspection and an output angle θo of specular light become small.

Likewise, in the surface defect inspection apparatus 300 according to the seventh embodiment, each unit is set so that the foregoing conditional expressions (4) to (7) are satisfied. The light reception unit (17 and 22 to 24) is a dirk field optical system relative to specular light and the illumination unit (11 to 13 and 17) and the light reception unit (17 and 22 to 24) are provided with polarization units 13 and 22, respectively. Thus, noise light (specular light, diffracted light, and so forth) that are not necessary to perform an inspection for a surface defect on the surface under inspection 5a can be securely removed.

In addition, since the polarization units 13 and 22 remove diffracted light that is emitted from the surface under inspection 5a, even if an optical axis of the diffracted light overlaps with an optical axis C4 of the light reception unit (17 and 22 to 24), the diffracted light can be securely removed and only scattered light that is emitted from a surface defect can be selected. As a result, an SN ratio necessary to perform an inspection for a surface defect can be securely obtained. In addition, even if there is a concave-shaped flaw on the surface under inspection 5a, scattered light can be securely generated therefrom. As a result, an SN ratio necessary to perform an inspection for a concave-shaped flaw can be securely obtained. Thus, the inspection for the surface defect can be properly performed.

Eighth Embodiment

Next, with respect to FIG. 13, an eighth embodiment of the present invention will be described.

As shown in FIG. 13, a surface defect inspection apparatus 400 according to the eighth embodiment includes a concave-shaped surface reflection mirror 18 instead of the large diameter lens 17 according to the seventh embodiment. In addition, polarization compensation plates 16 and 26 that are the same as those according to the sixth embodiment are diagonally inserted into optical paths between the concave-shaped surface reflection mirror 18 and the polarization units 13 and 22, respectively, In the surface defect inspection apparatus 400 according to the eighth embodiment, an illumination unit (11 to 13, 16, and 18) and a light reception unit (18, 22 to 24, and 26) share the concave-shaped surface reflection mirror 18. Thus, the structure of the apparatus is simplified. In addition, the surface defect inspection apparatus 400 becomes compact in size in comparison with the apparatus including the lens 17 according to the seventh embodiment.

Likewise, in the surface defect inspection apparatus 400 according to the eighth embodiment, each unit is set so that the foregoing conditional expressions (4) to (7) are satisfied. The light reception unit (18, 22 to 24, and 26) is a dirk field optical system relative to specular light and the illumination unit (11 to 13, 16, and 18) and the light reception unit (18, 22 to 24, and 26) are provided with polarization units 13 and 22, respectively. Thus, noise light (specular light, diffracted light, and so forth) that are not necessary to perform an inspection for a surface defect on the surface under inspection 5a can be securely removed.

In addition, since the polarization units 13 and 22 remove diffracted light that is emitted from the surface under inspection 5a, even if an optical axis of the diffracted light overlaps with an optical axis C4 of the light reception unit (18, 22 to 24, and 26), the diffracted light can be securely removed and only scattered light that is emitted from a surface defect can be selected. As a result, an SN ratio necessary to perform an inspection for a surface defect can be securely obtained. In addition, even if there is a concave-shaped flaw on the surface under inspection 5a, scattered light can be securely generated therefrom. As a result, an SN ratio necessary to perform an inspection for a concave-shaped flaw can be securely obtained. Thus, the inspection for the surface defect can be properly performed.

(Modifications of Fifth to Eighth Embodiments)

In the foregoing embodiments, an example of which the optical axis C4 of the light reception unit 20 is contained in the plane of incidence P1 (formed of the optical axis C1 of the illumination unit and the normal line C2 of the surface under inspection 5a) was described. However, it should be noted that the present invention is not limited to such an example. For instance, as shown in FIG. 9(a) viewed from arrow III in FIG. 10 and FIG. 3, a plane P2 containing the optical axis C3 of specular light and the optical axis C4 of the light reception unit 20 may be inclined to the plane of incidence P1 at a predetermined angle θs. In this case, the angle θr of the optical axis C4 of the light reception unit 20 is set so that the conditional expressions (6) and (7) are satisfied on the plane P2.

Instead, as shown in FIG. 9(b) viewed from arrow III in FIG. 10 and FIG. 3, the plane P3 containing the optical axis C3 of specular light and the optical axis C4 of the light reception unit 20 may have an angle θs=90 degrees relative to the plane of incidence P1. In this case, while the angle θr of the optical axis C4 is kept constant, the incident angle θi of the optical axis C1 of the illumination unit and the output angle θo of the optical axis C3 of specular light can be easily changed.

As shown in FIG. 9(a) and FIG. 9(b), when the planes P2 and P3 containing the optical axis C3 of specular light and the optical axis C4 of the light reception unit 20 are inclined to the plane of incidence P1, the angle θr of the optical axis C4 can be set by rotating (shaking) the light reception unit 20 itself around the axis AX3. The axis AX3 is an axis that passes through the intersection of the optical axis C1 of the illumination unit 10 and the surface under inspection 5a and that is perpendicular to the planes P2 and P3.

According to the foregoing embodiments, an example of which the polarization units 13 and 22 remove diffracted light that is emitted from the surface under inspection 5a was described. In addition to the polarization units 13 and 22, angle conditions may be adjusted in the following manner. The angle θr of the optical axis C4 of the light reception unit 20 is set to the smallest angle (that is close to the optical axis C3 of specular light) in an angle range that allows a dirk field optical system to be structured relative to specular light. In addition, the angle θr is set to an angle that allows a dirk field optical system to be structured relative to diffused light. These angular adjustments allow diffracted light to be more securely removed.

The output direction of diffracted light depends on pitches of repetitive patterns formed on the surface under inspection 5a and the wavelength of illumination light. Thus, by changing the wavelength of the illumination light, diffracted light can be prevented from being guided to the light reception unit 20. In this case, the wavelength of the illumination light is selectively set by the wavelength selection unit 12 of the illumination unit 10 and the diffraction angle is adjusted so that diffracted light is not guided to the light reception unit 20. In this case, however, the same wavelength selection unit may be disposed in the light reception unit so that the light reception side can select the wavelength of the diffracted light.

The invention is not limited to the above embodiments and various modifications may be made without departing from the spirit and scope of the invention. Any improvement may be made in part or all of the components.

What is claimed is:

1. A surface defect inspection apparatus, comprising:
    an illumination unit which illuminates a front surface of an object to be inspected with illumination light for inspection;
    a changing unit which relatively rotates said object to be inspected and said illumination unit around an axis perpendicular to said front surface, to change illumination conditions of said illumination light;
    a light reception unit which receives scattered light emitted from said front surface when said front surface is illuminated with said illumination light in each of said illumination conditions, to capture images of said front surface; and
    a combining unit which combines said images captured in different illumination conditions by said light reception unit, to generate a combined image.

2. The surface defect inspection apparatus as set forth in claim 1, wherein
    said changing unit relatively rotates said object to be inspected and said illumination unit at equal intervals within an angle range of 180 degrees or 360 degrees around the axis perpendicular to said front surface, to change said illumination conditions.

3. The surface defect inspection apparatus as set forth in claim 2, further comprising:
    an image processing unit which processes said combined image generated by said combining unit to detect a defect on said front surface.

4. The surface defect inspection apparatus as set forth in claim 2, further comprising:
    a display unit which displays said combined image generated by said combining unit.

5. The surface defect inspection apparatus as set forth in claim 1, wherein
    said light reception unit is set so as to satisfy following conditional expressions (1) to (3):

$$\delta\theta o < (\theta r - \delta\theta r) \quad (1)$$

$$\theta r \leq 10 \text{ degrees} \quad (2)$$

$$\theta o \leq 60 \text{ degrees} \quad (3)$$

where θo is an output angle of specular light emitted from said front surface when said front surface is illuminated with said illumination light; δθo is an aperture angle of said specular light; θr is an angle between an optical axis of said specular light and an optical axis of said light reception unit; and δθr is an aperture angle of said light reception unit.

6. The surface defect inspection apparatus as set forth in claim 5, wherein:
    the optical axis of said light reception unit is included in a same plane of incidence as those of said illumination unit and of said specular light; and
    at least one of said object to be inspected, said illumination unit, and said light reception unit is rotatably supported around an axis which runs through an intersection of the optical axis of said illumination unit and said front surface and is perpendicular to said plane of incidence.

7. The surface defect inspection apparatus as set forth in claim 6, further comprising:
    a setting unit which rotates at least one of said object to be inspected, said illumination unit, and said light reception unit around the axis perpendicular to said plane of incidence, to set the output angle θo of the specular light and the angle θr of the optical axis of said light reception unit.

8. The surface defect inspection apparatus as set forth in claim 1, wherein
said illumination light is substantially collimated light.

9. The surface defect inspection apparatus as set forth in claim 8, wherein:
said illumination light is linearly polarized light; and
said light reception unit receives a polarization component of the scattered light emitted from said front surface, to capture said images, the polarization component being perpendicular to a plane of vibration of said linearly polarized light.

10. The surface defect inspection apparatus as set forth in claim 8, wherein
said illumination unit and said light reception unit have telecentric structures on their respective sides facing to said front surface.

11. A surface defect inspection method, comprising the steps of:
illuminating a front surface of an object to be inspected with illumination light for inspection;
relatively rotating said object to be inspected and said illumination unit around an axis perpendicular to said front surface, to change illumination conditions of said illumination light;
receiving scattered light emitted from said front surface when said front surface is illuminated with said illumination light in each of said illumination conditions, to capture images of said front surface; and
combining said images captured in different illumination conditions at the light receiving step, to generate a combined image.

12. The surface defect inspection method as set forth in claim 11, wherein
the condition changing step further comprises the step of relatively rotating said object to be inspected and said illumination unit at equal intervals within an angle range of 180 degrees or 360 degrees around the axis perpendicular to said front surface, to change said illumination conditions.

13. A surface defect inspection apparatus, comprising:
an illumination unit which illuminates a front surface of an object to be inspected with linearly polarized light;
a changing unit which relatively rotates said object to be inspected and said illumination unit around an axis perpendicular to said front surface, to change illumination conditions of said illumination light; and
a light reception unit which receives a polarization component of scattered light emitted from said front surface when said front surface is illuminated with said linearly polarized light, the polarization component being perpendicular to a plane of vibration of said linearly polarized light, wherein:
said light reception unit is set so as to satisfy following conditional expressions (1) to (3):

$$\delta\theta o < (\theta r - \delta\theta r) \quad (1)$$

$$\theta r \leq 10 \text{ degrees} \quad (2)$$

$$\theta o \leq 60 \text{ degrees} \quad (3)$$

where $\theta o$ is an output angle of specular light emitted from said front surface when said front surface is illuminated with said illumination light; $\delta\theta o$ is an aperture angle of said specular light; $\theta r$ is a angle between an optical axis of said specular light and an optical axis of said light reception unit; and $\delta\theta r$ is an aperture angle of said light reception unit.

14. The surface defect inspection apparatus as set forth in claim 13, wherein
the optical axis of said light reception unit is included in a same plane of as those of said illumination unit and of said specular light.

15. The surface defect inspection apparatus as set forth in claim 14, wherein
said object to be inspected is rotatably supported around the axis perpendicular to said front surface.

16. The surface defect inspection apparatus as set forth in claim 13, wherein
a plane which includes the optical axis of said light reception unit and the optical axis of said specular light is inclined at a predetermined angle $\theta s$ to the plane which includes the optical axis of said illumination unit and the optical axis of said specular light.

17. The surface defect inspection apparatus as set forth in claim 16, wherein
said predetermined angle $\theta s$ is 90 degrees.

18. The surface defect inspection apparatus as set forth in claim 13, wherein
said object to be inspected is rotatably supported around the axis perpendicular to said front surface.

19. The surface defect inspection apparatus as set forth in claim 13, wherein
said linearly polarized light is substantially collimated light.

20. The surface defect inspection apparatus as set forth in claim 19, wherein:
said illumination unit illuminates the entire front surface with said linearly polarized light at once; and
said light reception unit receives a polarization component of scattered light emitted from the entire front surface, to capture an image of the entire front surface at once, the polarization component being perpendicular to a plane of vibration of said linearly polarized light.

21. The surface defect inspection apparatus as set forth in claim 19, wherein
said illumination unit and said light reception unit have telecentric structures on their respective sides facing to said front surface.

22. The surface defect inspection apparatus as set forth in claim 13, further comprising:
an image processing unit which processes an image generated by said light reception unit to detect a defect on said front surface.

23. The surface defect inspection apparatus as set forth in claim 13, further comprising:
a display unit which displays an image generated by said light reception unit.

* * * * *